(12) United States Patent
Migaly

(10) Patent No.: US 7,973,043 B2
(45) Date of Patent: Jul. 5, 2011

(54) COMBINATION THERAPY FOR DEPRESSION, PREVENTION OF SUICIDE, AND VARIOUS MEDICAL AND PSYCHIATRIC CONDITIONS

(76) Inventor: Peter Migaly, Blairsville, PA (US)

( * ) Notice: Subject to any disclaimer, the term of this patent is extended or adjusted under 35 U.S.C. 154(b) by 597 days.

(21) Appl. No.: 10/627,358

(22) Filed: Jul. 25, 2003

(65) Prior Publication Data

US 2004/0204401 A1    Oct. 14, 2004

Related U.S. Application Data

(60) Provisional application No. 60/319,436, filed on Jul. 30, 2002.

(51) Int. Cl.
| | |
|---|---|
| A61K 31/497 | (2006.01) |
| A61K 31/551 | (2006.01) |
| A61K 31/4025 | (2006.01) |
| A61K 31/519 | (2006.01) |
| C07D 243/14 | (2006.01) |
| C07D 419/14 | (2006.01) |
| C07D 207/09 | (2006.01) |

(52) U.S. Cl. .............. 514/255.05; 514/405; 514/427; 514/220; 514/259.41; 540/557; 544/405; 548/561

(58) Field of Classification Search .............. 514/259.31
See application file for complete search history.

(56) References Cited

U.S. PATENT DOCUMENTS

| | | | |
|---|---|---|---|
| 4,310,524 | A | 1/1982 | Wiech et al. |
| 5,500,343 | A | 3/1996 | Blum et al. |
| 5,589,512 | A | 12/1996 | Norden |
| 5,591,884 | A | 1/1997 | DeNinno et al. |
| 5,780,051 | A | 7/1998 | Eswara et al. |
| 5,958,921 | A * | 9/1999 | Tollefson ............ 514/220 |
| 6,066,643 | A | 5/2000 | Perry |
| 6,121,259 | A | 9/2000 | Yelle |
| 6,147,072 | A | 11/2000 | Bymaster et al. |
| 6,159,963 | A | 12/2000 | Beasley et al. |
| 6,174,882 | B1 | 1/2001 | Yelle |
| 6,322,503 | B1 | 11/2001 | Sparhawk, Jr. |
| 6,348,455 | B1 | 2/2002 | Yelle |
| 6,352,984 | B1 | 3/2002 | Yelle |
| 6,395,727 | B1 | 5/2002 | Guadagno et al. |
| 6,399,608 | B1 | 6/2002 | Dawson |
| 6,582,737 | B2 | 6/2003 | Hirsh et al. |
| 6,960,577 | B2 | 11/2005 | Tollefson |
| 2001/0048943 | A1 | 12/2001 | Faour et al. |
| 2002/0016325 | A1 | 2/2002 | Taylor |
| 2002/0035145 | A1 | 3/2002 | Tsai et al. |
| 2002/0040041 | A1 | 4/2002 | Taylor |
| 2002/0051807 | A1 | 5/2002 | Faour et al. |
| 2002/0123490 | A1* | 9/2002 | Howard, Jr. ............ 514/220 |
| 2003/0049308 | A1* | 3/2003 | Theobald et al. ............ 424/449 |

FOREIGN PATENT DOCUMENTS

| | | |
|---|---|---|
| EP | 0958824 A2 | 11/1999 |
| EP | 0958824 A2 | 11/1999 |
| EP | 0966967 A2 | 12/1999 |
| EP | 1238676 A1 | 9/2002 |
| WO | WO 95/00154 | 1/1995 |
| WO | WO 99/58130 | 11/1999 |
| WO | WO 99/61027 | 12/1999 |
| WO | WO 01/51040 | 7/2001 |
| WO | WO 01/51041 | 7/2001 |
| WO | WO01/80837 | * 11/2001 |
| WO | WO 02/053140 A2 | 7/2002 |
| WO | WO02/060423 | * 8/2002 |

OTHER PUBLICATIONS

U.S. Appl. No. 10/001,827, filed Jul. 2002, Chappell et al.*
George, t. et al. "A Placebo-Controlled Trial of Bupropion for Smoking Cessation in Schizophrenia" (2002) Biological Psychiatry, vol. 52, pp. 53-61.*
Kelleher et al., "Advances in Atypical Antipsychotics for the Treatment of Schizophrenia" CNS Drugs (2002) vol. 16, No. 4, pp. 249-261.*
Berman et al., "Antidepressant Effects of Ketamine in Depressed Patients," Biological Psychiatry (2000) vol. 47, pp. 351-354.*
Robertson et al., "Major Tranquilizers Used as Antidepressants" Journal of Affective Disorders (1982) vol. 4, pp. 173-193.*
Chemical Abstracts Registry entry No. 129722-12-9 (aripiprazole), entered into STN on Oct. 5, 1990.*
The Merck Manual of Diagnosis and Therapy, Seventeenth Edition, published 1999 by Merck Research Laboratories, ed. by Beers and Berkow, pp. 1531-1538 and 1569-1570.*
Pivac et al., "Collegium Internationale Neuro-Psychopharmacologicum" Psychiatria Danubina (2002) vol. 14, No. 3-4, pp. 231-242.*
Roth et al., "D4 Dopamine receptor binding affinity does not distinguish between typical and atypical antipsychotic drugs," Psychopharmacology (1995) vol. 120, pp. 365-368.*
Schmidt et al., "Ziprasidone: a novel antipsychotic agent with a unique human receptor binding profile" European Journal of Pharmacology (2001) vol. 425, pp. 197-201.*
American Academy of Pediatrics, Committee on Nutrition, "The Use and Misuse of Fruit Juice in Pediatrics" Pediatrics (2001) vol. 107, No. 5, pp. 1210-1213.*

(Continued)

Primary Examiner — Eric S Olson

(57) ABSTRACT

The present invention relates to a new method of treatment for persons meeting diagnoses for major depressive disorder, or other unipolar (non-bipolar, non-psychotic and non-treatment resistant) depression. The method comprises administering a combination of two categories of drugs, antipsychotics or dopamine system stabilizers, in combination with a newer antidepressant such as a selective serotonin reuptake inhibitor, as initial treatment or as soon as possible. The method targets the prevention of suicide, and provides other benefits including preventing disease progression development of tolerance toward the antidepressants. Another aspect of the invention relates to using the method for alleviating cognitive distortion and related functional impairment or health risks, and/or using the method for smoking cessation or nicotine withdrawal.

133 Claims, No Drawings

OTHER PUBLICATIONS

Casey et al., "An integrated cognitive model of panic disorder: The role of positive and negative cognitions" Clinical Psychology Review (2004) vol. 24 pp. 529-555.*
WHfoods, "Is Fruit Juice as good as whole fruit" published online at http://www.whfoods.com/genpage.php?tname=george&dbid=74.*
Ost et al., "Probability ratings in claustrophobic patients and normal controls" Behavior Research and Therapy (2000) vol. 38 pp. 1107-1116.*
Tang et al., PNU-96415E, a Potential Antipsychotic Agent with Clozapine-Like Pharmacological Properties The Journal of Pharmacology and Experimental Therapeutics (1997) vol. 281, pp. 440-447.*
Uhlenhuth et al., "The revised Anxious Thoughts and Tendencies (AT&T) scale: a general measure of anxiety-prone cognitive style" Journal of Affective Disorders (1999) vol. 52, pp. 51-58.*
WHfoods, "Is Fruit Juice as good as whole fruit" published online at http://www.whfoods.com/genpage.php?tname=george&dbid=74 Aug. 25, 2008.*
Michael E. Thase, M.D.; "What Role Do Atypical Antipsychotic Drugs Have in Treatment-Resistant Depression?"; The Journal of Clinical Psychiatry; Feb. 2002; pp. 95-103; 63:2; Physicians Postgraduate Press, Inc., Memphis, Tennessee.
Jambur Ananth; "Treatment-Resistant Depression"; Psychother Psychosom; 1998; pp. 61-70; 67; S. Karger AG, Basel, Switzerland.
D. Souery et al.; "Treatment resistant depression: methodological overview and operational criteria"; European Neuropsychopharmacology; 1999; pp. 83-91; 9; Elsevier Science B.V./ECNP; Amsterdam, The Netherlands.
Mark W. Viner, M.D. et al.; "Low-dose Risperidone Augmentation of Antidepressants in Nonpsychotic Depressive Disorders with Suicidal Ideation"; Journal of Clinical Psychopharmacology; Feb. 2003; pp. 104-106: vol. 23. No. 1; Lippincott Williams & Wilkins; Philadelphia, Pennsylvania.
De Adson, M.D. et al.; "An Open Trial of Quetiapine for Anxiety in Patents Receiving an SSRI"; Society of Biological Psychiatry Annual Meeting; May 16-18, 2002; Philadelphia, Pennsylvania.
Shigehiro Hirose, M.D. and Charles R. Ashby, Jr., Ph.D.; "An Open Pilot Study Combining Risperidone and a Selective Serotonin Reuptake Inhibitor as Initial Antidepressant Therapy"; Journal of Clinical Psychiatry; Aug. 2002; pp. 733-736; 63:8; Physicians Postgraduate Press, Inc., Memphis, TN.
Evins at al. Buproprion and smoking cessation (Am. J. Psychiatry 156:5, May 1999 pp. 798-799.).
Beasely CM et al Olanzapine versus placebo and Haloperidol. Acute phase results of the North American double-blind olanzapine trial. Neuropsychopharmacology 14: 111-123 1996.
Tollefson GD et al (1998a) Depressive signs and symptoms in Schizophrenia. A prospective blinded trial of olanzapine and haloperidol. Arch Gen Psychiatry 1998; 55:250-258.
Tollefson GD et al (1998b) A double-blind, controlled comparison of the novel antipsychotic olanzapine versus haloperidol or placebo on anxious and depressive symptoms accompanying schizophrenia. Biol Psychiatry 1998; 43:803-810.
Azhar MZ Comparison of fluvoxamine alone, fluvoxamine and cognitive psychotherapy and psychotherapy alone in the treatment of panic disorder in Kelantan—implications for management by family doctors. Med J Malaysia 2000 55(4)402-8.
Barlow DH Anxiety and its disorders (learned alarms) pp. 220-225, Guilford Press,1988.
Brody A. et al Regional brain metabolic changes in patients with major depression treated with either paroxetine or Interpersonal therapy. Arch Gen Psychiatry 2001; 58:631-640.
Cremers TI, et al Is the beneficial antidepressant effect of coadministration of pindolol really due to somatodendritic autoreceptor antagonism? Biol Psychiatry Jul. 1, 2001; 50(1):13-21. Current Patents Nov. 15, 2002 week 0246 at http://scientific.thompson.com/media/cdjournals/gazettenews/202/CPG_News_0246.pfd-enclosed.].
DeRubeis RJ et al Cognitive therapy vs Medications in the treatment of moderate to severe depression Arch Gen Psychiatry 2005; 62:409-416.

Ferris RM et al Buproprion: a new antidepressant drug, the mechanism of action of which is not associated with downregulation of postsynaptic β-adrenergic, serotonergic (5-HT2), α2-adrenergic, imipramine and dopaminergic receptors in brain. Neuropharmacology 22 No. 11, 1257-1267, 1983.
Goldapple K. et al Modulation of cortical-limbic pathways in major depression. Arch. Gen Psychiatry, vol. 61, Jan. 2004, pp. 34-41.
Kramer MS et al The effects of a selective D4 dopamine receptor antagonist (L-745,870) in acutely psychotic inpatients with schizophrenia. Arch Gen Psychiatry 1997; 54:567-572.
Kuoppamaki M et al Differential regulation of rat 5-HT2A and 5-HT2C receptors after chronic treatment with clozapine, chrorpromazine and three putative atypical antipsychotic drugs. Neuropsychopharmacology 13:139-150, 1995.
Landen M. et al A randomized, double-blind, placebo-controlled trial of buspirone in combination with an SSRI in patients with treatment-refractory depression. J. Clin Psychiatry 1998; 59:664-668.
Paton, C. Generic clozapine: outcomes after switching formulations. British Journal of Psychiatry 2006. 189 184-185.
Perez V et al A double-bind, randomized, placebo-controlled trial of pindolol augmentation in depressive patients resistant to serotonin reuptake inhibitors. Arch Gen Psychiatry. 1999; 56(4):375-379.
Roth BL et al Chronic mianserine treatment decreases 5-HT2 receptor binding without altering 5-HT2 receptor mRNA levels. European Journal of Pharmacology—Molecular Pharmacology Section, 207 (1991) 169-172.
Sharp DM et al Global measures of outcome in controlled comparison of pharmacological and psychological treatment of panic disorder and agoraphobia in primary care. Br J Gen Pract 1997 47(416) 150-5.
Simon NM et al (Longitudinal outcome with pharmacotherapy in a naturalistic study of panic disorder. Journal of Affective Disorders 69 (2002) 201-208.
Stoner, S.C. et al A program to convert patients from Trade-name to generic clozapine Pharmacotherapy 2003; 23(6):806-810 [particularly p. 806 second col. $3^{rd}$ line from the bottom on patent expiration.
Toth M et al Antagoist-mediated downregulation of 5-hydroxytryptamine type 2 receptor gene expression: Modulation of transcription. Molecular pharmacology 45:1095-1100, 1994.
Van Putten T. The many faces of akathisia Comprehensive psychiatry vol. 16 (1) 1975 43-47.
Zubenko G et al Antidepressant-related akathisia J Clin Psychopharmacol vol. 7(4) 1987 254-257.
Lipinski J F. et al Fluoxetine-induced akathisia: Clinical and theoretical implications. J Clin Psychiatry 50:9 1989 339-342.).
Nair, NPV et al Neurochemical and receptor theories of depression. Psychiat J. Univ Ottava, vol. 14(2) 1989 pp. 328-341 p. 328 first column lines 3-5 and 9-10.).
Reeves H et al, Efficacy of risperidone augmentation to antidepressants in the management of suicidality in major depressive disorder: a randomized, double-blind, placebo-controlled pilot study. J Clin Psychiatry 69:8 2008 1228-1236. p. 1229 first col. 9-10.
Roya Karoum F et al Marked reduction in indexes of dopamine metabolism among patients with depression who attempts suicide. Arch Gen Psychiatry 49, 1992 447-450. Page 447 last two lines of first column and first two of second one, and p. 448 last four lines of second column.
Hirsch SR et al The concept and efficacy of the treatment of parasuicide. Br J. clin Parmac 1983, 15, 189S-194S table 1 on p. 189S.
Poyurovsky M et al Mirtazapine for the neuroleptic-induced akathisia. Am J psychiatry 158:5 2001 p. 819 second paragraph first sentence.
Hirose S et al. An open pilot study combining risperidone and a selective serotonin reuptake inhibitor as initial antidepressant therapy. J. Clin Psychiatry vol. 63, (8) Aug. 2002, pp. 733-736.
Barbee J G et al's article Lamotrigine as an augmentation agent in treatment-resistant depression. J.Clin Psychiatry 63:8 Aug. 2002 p. 737-741.
Evins at al. Am. J. Psychiatry 156:5, May 1999 pp. 798-799.
Battaglia J et al Structured assessment and depot fluphenazine treatment of multiple suicide attempters in the emergency department. International Clinical Psychopharmacology 1999, 14: 361-372.

Steiner M. The neurochemistry of mood, Psychiat J. Univ Ottava, vol. 14(2) 1989 pp. 342-343. p. 342 first column lines 5-8.

Montgomery SA et al Br J. clin Parmac 1983, 15, 183S-188S, p. 183S second column second paragraph, and p.185S first column third paragraph.

Van Putten T et al Behavoral toxicity of antipsychotic drugs, J Clin Psychiatry 48 [9, Suppl]:13-19, 1987.

Drake RE et al Suicide attempts associated with akathisia Am J Psychiatry 142:4, Apr. 1985.

Shear, M.K. e al Suicide associated with akathisia and depot fluphenazine treatment. Journal of Clinical Psychopharmacology vol. 3 (4) 1983 235-236.

Blum A Patients at risk of developing severe side effects from depot fluphenazine treatment Am J Psychiatry 137:2 1980 254-255.

Shaw ED et al A case of suicidal and homicidal ideation and akathisia in a double-blind neuroleptic crossover study J clin psychopharmacol vol. 6(3) 1986 196-197.

Smith WT et al. Short term augmentation of fluoxetine with clonazepam in the treatment of depression: A double-blind study. Am J Psychiatry 155:10 1998 1339-45.

Tsai G E. A new class of antipsychotic drugs Enhancing neurotransmission by NMDA receptors Psychiatric Times Dec. 2008, p. 16-18.

Viner MW et al Low-dose risperidone augmentation of antidepressants in nonpsychotic depressive disorders with suicidal ideation. Journal of Clinical Psychopharmacology 23:1 2003).

Reeves H et al Efficacy of risperidone augmentation to antidepressants in the management of suicidality in major depressive disorder: a randomized, double-blind, placebo-controlled study. J. Clin Psychiatry 69:Aug. 8, 2008).

Texas Algorithm Jul. 2004 Arch Gen Psych p. 671 http://archpsyc.ama-assn.org/cgi/content/abstract/61/7/669—see within the reply and next.

Clinical Results for Patients With Major Depressive Disorder in the Texas Medication Algorithm Project M. H. Trivedi; A. J. et al. Arch Gen Psychiatry. 2004;61:669-680.

Berlin Algorithm Project—in Aldi 2003 [listed below under #2 and at p. 6 of our reply].

Algorithm Study of the German Research Network on Depression—in Aldi 2003 [listed below under #2 and at p. 7 of our reply].

STAR*D—(stepwise treatment procedures in depression)—NIMH funded study—in Aldi 2003 [listed below under #2 and at p. 8 of our reply].

Aldi, M. et al Algorithms for optimizing the treatment of depression: Making the right decisions at the right time. Pharmacopsychiatry 2003; 36 Suppl 3: S222-S229.

See also: http://www.charite.de/psychiatrie/publikationen/2003.html (2003).

Interview with Russel Katz director of neuropharmacological drug products at the FDA—Tribune Review Mar. 23, 2004 (Antidepressants . . . ).

Interview with Robert Temple director of FDA's Office of Medical Policy—Pittsburgh Post-Gazette Dec. 14, 2006 (FDA may expand alert . . . ).

* cited by examiner

COMBINATION THERAPY FOR DEPRESSION, PREVENTION OF SUICIDE, AND VARIOUS MEDICAL AND PSYCHIATRIC CONDITIONS

CROSS-REFERENCE TO RELATED APPLICATION

This application claims priority under 35 USC §119(e) to Provisional Application Ser. No. 60/319,436, filed Jul. 30, 2002, entitled "New Approaches to the Treatment, Assessment and Research of Depression", explicitly incorporated herein by reference.

FIELD OF THE INVENTION

The present invention relates to a new method of treatment for persons diagnosed with unipolar depression, including major depressive disorder, dysthymic disorder, and/or dual depression. The method may also be used to treat depression NOS, substance/alcohol induced mood disorder (depression), postpartum depression, adjustment disorder with depressed mood, cognitive distortions, smoking cessation or nicotine withdrawal.

The method comprises administering an antipsychotic drug, preferably an a typical antipsychotic or dopamine system stabilizer, in combination with a newer antidepressant such as a selective serotonin reuptake inhibitor, or other newer antidepressants.

BACKGROUND INFORMATION

The rate of depression has been rising over the years. It affects 17.6 million Americans every year, robbing people of a fulfilling life with a cost of about $44 to $52.9 billion annually. It carries the risk of suicide with 30,000 to 35,000 deaths a year, a rate that resembles the death rate from leukemia.

The first treatments for severe mental disturbances became available in the 1930's, when extracts from the plant rauwolfia serpentina were used for the amelioration of psychotic symptoms. Major advances in the treatment of psychosis, however, did not come until 1950 with the discovery of chlorpromazine. The first generation of antidepressants did not become available until the 1950's, and included monoamine oxidase inhibitors and tricyclic antidepressants. While chlorpromazine was used early on in the treatment of depression, as tricyclic antidepressants became available the use of antipsychotic medications declined, and they were never widely used in the treatment of depression in the absence of psychotic symptoms. See also Raskin A. et al 1970, p.170: "There is a persistent belief that these drugs (antipsychotics) are not very effective in the treatment of depression". In general, the use of antipsychotic drugs was reserved for use in patients having psychotic symptoms. It was generally accepted that antipsychotic drugs used alone could not treat major depressive disorder. In fact, it was thought that antipsychotic drugs, including some of the a typical antipsychotics, may even have depressogenic properties. (Harrow, M. et al 1994, Galdi J. 1983, Tollefson, G. D. et al 1998, Maguire, G. A. 2002, Cookson I. B. et al.)

In contrast to antidepressants, antipsychotics alone (including the a typical antipsychotic risperidone) were ineffective in the chronic mild stress (CMS) model (animal simulation of depression) (Papp, M. et al 1996; Papp, M. et al 2000).

In sum, many studies showed that antipsychotics do not have significant antidepressant activity and, if anything, may cause a depressogenic effect.

Due to the severe side effect profiles of the traditional antipsychotic drugs, the risks of taking these drugs, in the absence of their specific indications (such as psychosis, severe agitation or anxiety) were believed to be unwarranted by the medical community. (Price, L. H. et al. 2001. p. 207.)

Such risks included side effects such as tardiv dyskinesia (TD), a potentially irreversible effect involving involuntary movement or other dyskinetic movements, or the rare but potentially fatal neuroleptic malignant syndrome (NMS). Many states (e.g. MN) require written consent forms from patients prior to starting an antipsychotic medication in inpatient psychiatric settings, and some outpatient clinics have also adapted that policy.

Early reports compared the antidepressant efficacy of two older/traditional groups of medications, the tricyclics (TCA) and traditional antipsychotics, or their use in combination, (Robertson, M., et al. 1982; Hollister, 1967). This review by Robertson (Robertson, M. M. et al. 1982) was based mostly on studies with mixed-anxiety depressive states, now more appropriately called as depression with anxiety as a comorbid disorder (Zimmerman, 2002). The combination use had been reserved for psychotic depression. A later review summarized the opinion, that "while a 'true' antidepressant effect has been demonstrated for the tricyclic antidepressants, similar effects appear doubtful for the antipsychotic drugs." (Nelson, J. C., 1987).

The combination use of these medications to treat non-treatment resistant, and non-psychotic depression was never recommended. A book chapter reviewing this topic from year 2001 makes the point that "the risk/benefit ratio in refractory patients lacking such features [as near-psychotic rumination or marked psychomotor agitation] generally does not favor [antipsychotic augmentation ]". (Price, H. 2001,). The reports available up to date have reserved the combination use of antidepressant-antipsychotics only for psychotic depression, or for treatment-resistant depression.

More recently, with the development of new a typical antipsychotic medications, there have been reports of using an a typical antipsychotic in combination with an antidepressant, such as an SSRI (selective serotonin reuptake inhibitor), to treat a specific subgroup of depressed patients that do not respond to antidepressants alone, that is, patients who have treatment-resistant depression (TRD). See, for example, WO 99/61027, which describes the use of SSRI's and a typical antipsychotics for partially-responding or treatment-resistant depression. Shelton, C. R., et al: 2001; Ostroff, R. B. et al: 1999; Alpert, J. E., et al.: 2002; Parker, G., 2002; Pitchot, W., et al 2001; O'Connor, M. 1998; Kaplan, M. 2000. See also reviews on the combined use of a typical antipsychotics and SSRIs for treatment resistant depression (Thase 2002). Nierenberg (Nierenberg. A. A., 1992) had noted that the cause of treatment-resistant depression may be an unrecognized psychosis, that may explain—at least in part—of why the "treatment-resistant" depression group improved with the addition of an antipsychotic medication.

As used herein, the term "treatment-resistant" is used as that term is understood by one skilled in the art, and as used in the present invention, means a lack of therapeutic response after at least one trial of an antidepressant at an adequate dose for six weeks.

While the newer drugs referred to as a typical antipsychotics have improved side effect profiles as compared with traditional antipsychotics, especially as regards to NMS, TD and acute extrapyramidal symptoms (EPS), they too can produce undesirable side effects, including potentially serious adverse effects not always present with some of the typical (older) antipsychotics. These adverse effects include agranulocytosis, (specifically with clozapine), neutropenia, seizure, weight gain, hyperglycemia, diabetes, diabetic ketoacidosis as a first sign of diabetes, hyperlipidemia/hypercholesterolemia, hyperprolactinamia (with potential consequent bone loss, depressive effect, and sexual dysfunction), orthostatic hypotension, tardive dyskinesia (TD) an involuntary movement, EPS, NMS, in EKG a prolongation of QTC interval with the potential of life threatening arrhythmia (ziprasidone), and other adverse effects (dry mouth, sedation, increase in appetite, asymptomatic elevations in liver enzymes, hypersalivation, tachycardia, hypotension, hypertension, constipation, and urinary incontinence). In addition, there are also some rare side effects associated with the a typical antipsychotics, such as priapism, rabbit syndrome, chorea, eosinophilia, Pisa syndrome, periodic leg movements and restless legs syndrome, and sudden death in patients receiving clozapine. There have also been reports of mania, and withdrawal syndromes.

Therefore, when combining antipsychotics with antidepressants it should be noted that some of their adverse effects may add up, or may present with new risks. These added or new risks may include the increase in weight; risk factor for diabetes, cardiac and other medical morbidity and mortality; hyponatremia, an electrolyte disturbance; TD; akathisia and extrapyramidal symptoms (EPS); and the potentially dangerous serotonin syndrome.

The a typical antipsychotics and dopamine system stabilizers are also expensive drugs. Thus, to date, the use of a typical antipsychotic medications has been restricted to their use in combination with antidepressants, for the treatment of the following subtypes of illness: schizoaffective disorder; psychotic depression; bipolar (manic-depressive) disorder; and treatment-resistant depression. In all of these categories, the use of antipsychotic medication may be expected due to its effects on contributory psychosis, or severe agitation.

There have been no reports recommending that the combination therapy can or should be used for a major depressive disorder, or for other depressions as an initial treatment, upon initial presentation to a health care provider (or as soon as possible), or for using the combination as a treatment of first choice, for reducing the risk of suicide.

Standard therapeutic methods of treating persons suffering from various types of depression, including major depressive disorder, who are at risk for suicide, and in particular those who are at high risk of suicide remain inadequate. There remains a need for an initial form of treatment to reduce the risk of suicide and other pathologies associated with depression, and in particular with major depressive disorder.

Effective methods of treating the symptoms associated with smoking cessation and nicotine withdrawal are similarly lacking. Unfortunately, smoking cessation rates at 1 year are very low, for the nicotine transdermal system (patch) it is 16.4%, for buproprion (Zyban) it is 23-30% (and with their combination is still only 28-35%). The smoking cessation rate is low even with the educational programs by the American Lung Association (19.0%-24.8%) or by the American Cancer Society (12.1-22.4%) (Migaly, P. smoking cessation book in progress). Therefore there is a need for improvement.

Different aspects of smoking cessation and treatment of nicotine withdrawal had been addressed before. U.S. Pat. No. 5,780,051 addresses the issue of antidepressants (including bupropion) with some other criteria; U.S. Pat. No. 6,582,737 addresses the use of bupropion with different criteria. U.S. Pat. No. 5,780,051 addresses the issue of antipsychotics including olanzapine, with some other criteria, and U.S. Pat. No. 6,159,963 also addresses the use of olanzapine in the treatment of nicotine dependence, and for withdrawal syndrome, again together with some other criteria.

None of the prior art has suggested the combination of low dose a typical antipsychotics or dopamine system stabilizers with newer antidepressants for treatment of smoking cessation and nicotine withdrawal, or the need to target cognitive distortions with this combination. However, the combination of these categories of medications are likely to potentiate each other and to provide an increased effectiveness.

SUMMARY OF THE INVENTION

The present invention addresses the above need and provides a method of treating persons having depression, major depressive disorder and, in particular, those at high risk of suicide. The method comprises administering an effective amount of an antipsychotic medication or dopamine system stabilizer in combination with a newer antidepressant, to patients who have not been diagnosed as treatment-resistant, or bipolar disorder, and who do not have psychotic symptoms. Preferably the antipsychotic medication is an a typical antipsychotic. In one embodiment, the antidepressant is a selective serotonin reuptake inhibitor. Furthermore, this combination may specifically target the prevention of suicide.

The present invention provides the following benefits: preventing disease progression/modifying the course of depression, delaying/preventing relapse or recurrence of depression, preventing the development of delusional/psychotic depression, being protective/(and/or) remedying the development of tolerance toward the antidepressant, and a possibility for providing a neuroprotective effect. It may also provide a more effective treatment, increase the response rate to treatment, treat the residual symptoms of depression, prevent the antidepressant's paradoxical effect of sensitizing patients to depression and relapse, and prevent the worsening of depression caused by the antidepressants.

It is an object of the present invention, therefore, to provide a method of initial treatment of a patient suffering from major depressive disorder, by administering an antipsychotic medication or a dopamine system stabilizer, in combination with a newer antidepressant.

It is a further object of the present invention to provide a method of treatment for major depressive disorder, in a patient who meets the diagnostic criteria, (or the depression types covered in this invention,), but is not on an antidepressant yet, or has not been in treatment long enough or does not meet criteria otherwise for treatment-resistant depression, or psychotic depression. The method comprises administering the combination of antidepressant—a typical antipsychotic, or antidepressant-dopamine system stabilizer medications, started as soon as possible, as an initial treatment.

It is an additional object of the present invention to provide a method of treating a patient suffering from unipolar depression, including major depressive disorder, to reduce the risk of suicide.

In an additional aspect, the present invention provides a method of treating a patient where the patient may or may not have any depression, the method comprising administering to said patient an effective amount of a newer antidepressant in combination with a low dose of an antipsychotic drug, a typical antipsychotic drug, or a dopamine system stabilizer; wherein treatment is given to decrease cognitive distortions, to alleviate related functional impairment or serious health hazards, and provide benefit in any and all of the corresponding disorders, to which cognitive distortions contribute.

In yet another additional aspect, the present invention provides a method of treating a patient where the patient may or may not have any depression, the method comprising administering to said patient an effective amount of a newer antidepressant in combination with a low dose of an antipsychotic drug, a typical antipsychotic drug, or a dopamine system stabilizer; wherein treatment is given for smoking cessation or nicotine withdrawal.

These and other objects of the invention will become more readily apparent from the following detailed description and appended claims.

DETAILED DESCRIPTION OF PREFERRED EMBODIMENTS

The present invention provides a method for initial treatment of a patient suffering from major depressive disorder, or other unipolar depression, including but not limited to, dysthymic disorder, dual depression, depression NOS, substance/alcohol induced mood disorder (depression), postpartum depression, adjustment disorder with depressed mood. As used herein, the term "unipolar depression" will refer to any of these types of depression. The method can also be used for treatment of cognitive distortions, smoking cessation or nicotine withdrawal. The method comprises administering an effective amount of a newer antidepressant in combination with an antipsychotic drug, to a patient in need of such treatment. In a preferred embodiment, the antidepressant is an SSRI, and the antipsychotic drug is an a typical antipsychotic drug, or a dopamine system stabilizer. Most preferably, the combination comprises fluoxetine and risperidone. Specifically, the patient is not treatment resistant, as that term is understood in the art, and does not have psychotic symptoms, such as delusions or hallucinations.

Excluded from the depression types covered under the present invention are bipolar (manic-depressive) disorder, delusional or psychotic depression, depression with psychotic features, depression occurring in psychotic disorders, and treatment-resistant depression.

In one embodiment the antidepressant can be any of the newer antidepressants, and the antipsychotic can be any of the a typical antipsychotics or dopamine system stabilizers.

In yet another embodiment, the antidepressant can be any of the newer antidepressants and the antipsychotic medication can be switched later to a dopamine system stabilizer. This can occur through tapering off or the sudden discontinuation of the antipsychotic with the start of the dopamine system stabilizer; or through a "cross taper" over a period of a time.

If an antipsychotic is used with a newer antidepressant, then it should be preferably given at a low dose and selected to also have a strong anxiolytic property. A low potency antipsychotic such as perphenazine (Trilafon) at a low dose is an option if the a typical antipsychotic or dopamine system stabilizer cannot be used. High potency antipsychotics have a particularly high risk for TD. Trifluoperazine (Stelazine) (at a low dose) may be considered to be a substitute if used for a short time. Haloperidol (Haldol) is not recommended as a preferred application as it is likely to be depressogenic.

Other antipsychotics (with some unusual characteristics) like amipsulpride, sulpiride or flupenthixol, that do not meet the a typical criteria of higher serotonin to dopamine affinity, may also be used in combination with antidepressants as an initial treatment.

It is thought that initial treatment of an individual suffering from major depressive disorder with the combination therapy of the present invention can dramatically reduce the risk of suicide, and provide many other advantages.

In particular, it is thought that the present combination therapy is especially beneficial in persons diagnosed with major depressive disorder and in persons with unipolar depression, who have thoughts of suicide, or are at risk of suicide. Those patients who present in acute settings, like in ER, would be particularly good candidates for the combination therapy. However, all depressed patients are at risk of suicide.

As used herein, "effective amount" means the amount of drug necessary to provide a therapeutic benefit, such as substantial improvement in mood and relief from symptoms of depression, the amount necessary to provide prevention of suicide, or to achieve the other benefits of the combination listed above. Determination of the appropriate dosage is well within the ability of one skilled in the art; antidepressants and antipsychotics have been prescribed for years. When used in the combination of the present invention, dosage of the antidepressant will be similar to the dosage amount needed when prescribed alone, while the amount of antipsychotic drug needed will be somewhat less than the amount used when that class of drug is prescribed alone for a patient experiencing psychotic symptoms. In the method of the present invention, the dosage of the antipsychotic drug should be around approximately one-third (⅓) to the average dose of the amount normally prescribed. However, a lower than average dose is preferred for most cases. At times minimal dose can be expected to be sufficient, like for quetiapine 25-50 mg, (if needed raised up to 300-400 mg q.d.), for risperidone 0.5-1 mg (if needed raised to 2-4 mg q.d.), for olanzapine 2.5 mg-5 mg, (and at times used at 10 mg q.d.), or for ziprasidone 10-20 mg (at times at 40 mg), and most likely, for aripiprazole 2.5-10 mg q.d. or less; (if needed given at 15 mg q.d.) as an example.

It should also be understood that these doses are not fixed, and a lower dose may be effective for some, but not for others. In the case of the a typical antipsychotics and dopamine system stabilizers, a higher dose (similar to the doses given for psychosis) may be effective in the prevention of suicide. The exceptions from this are the doses when EPS and other side effects occur. However, it is best to expose the patient to the least amount of effective medication. In addition lower doses may have other benefits as well.

Suitable dosage forms include capsules, tablets, and the like, preferably for oral administration, although any dosage form, for any route of administration is contemplated. The combination therapy can be administered as separate entities, e.g. two tablets or other forms, each containing one drug, or may be administered as a single dosage form containing both drugs (i.e. within the same delivery system), or concomitant use, (e.g. within 5 minutes).

In case of oral administration of the different medication components, the single dose can be, but is not limited to a (single) capsule, tablet (including "sprinkle", fast dissolving, "melt away",), or oral solution, and it may also contain inactive component(s) that is necessary to form the single delivery system.

The medications (with different medication components) can also be administered by other routes, not limited to oral intake. For example, administration can be transdermal (patch), buccal, sublingual, topical, nasal, parenteral (subcutaneous, intramuscular, intravenous, intradermal,), rectal, vaginal, administration. Various combinations of controlled release/rapid release are also contemplated.

As used herein, the term "partial response" is used as that term is understood in art, and refers to 25-49% improvement from baseline on recognized depression rating scales (Hirschfeld, R. M. A. et al 2002). Response to treatment refers to an improvement of at least 50% in depression scales, and non-response refers to improvement of less than 25% (Hirschfeld, R. M. A. et al 2002).

It is possible to have a response to an antidepressant treatment (i.e. better than a partial response or non-response), but still have residual symptoms, and not a full recovery. Therefore the combination may also be effective to treat residual symptoms of depression (which is a separate entity and not equal to partial response), to achieve full remission as a goal. In this case the risk/benefit analysis of giving a medication combination is also different from TRD.

Major depressive disorder may also be accompanied by many relapses. The combination treatment of the present invention may delay or prevent relapse, be prophylactic for the recurrence of depression; prevent disease progression and modify the course of depression. The combination treatment may also prevent the progression of the disease and modify the course of depression by preventing the development of delusional/psychotic depression; or by being protective against, and/or remedying the development of tolerance toward the antidepressant, when the antidepressant has lost its effectiveness.

In addition, depression may emerge during treatment with antidepressants in non-depressed patients (Fux, M. et al 1993, Fava, G. A. 2003,), and antidepressants may have a paradoxical effect and may be sensitizing patients to depression or relapse. (DiMascio, A. et al 1968, Fava, G. A. 2003). The combination treatment may also be protective for this phenomenon. The combination treatment may help avoiding the worsening of depression caused by the antidepressants.

As used herein, the term "major depressive disorder" (MDD) is used as that term is understood in art, and refers to a diagnosis that is guided by diagnostic criteria listed in DSM-IV or ICD-10, or in similar nomenclatures. (DSM-IV-TR., 2000, Kaplan, H. I. et al. 1998.) There are also some exclusion criteria for both the major depressive episode, and MDD. Major depressive episode can be a building block to diagnose MDD and other mood disorders (e.g. bipolar disorder), and it is not specific to MDD. However, DSM IV requires for the diagnosis of MDD the presence of a major depressive episode. This in turn consists of at least five of the nine symptoms present during the same 2-week period, of which depressed mood or loss of interest or pleasure has to be one of the symptoms. Changes in weight/appetite, sleep, energy, psychomotor retardation or agitation, guilt, decreased concentration, suicidality are the other symptoms. One does not need to have all of the symptoms present for the diagnosis, and MDD or major depressive episode is therefore not equal to the individual symptoms, as some may be absent. Suicidal thought is one of the depressive signs tested and need not to be present for the diagnosis of MDD.

The definition of other diagnostic terms referenced here are also used as they are understood in the art, and refer to diagnoses that are guided by diagnostic criteria listed in DSM-IV or ICD-10, or in similar nomenclatures. (DSM-IV-TR., 2000, Kaplan, H. I. et al. 1998.)

It should also be noted that depression is not the only psychiatric disorder leading to suicide. Other disorders like bipolar disorder, psychotic disorders (like schizophrenia), anxiety disorders (including panic disorders, OCD, PTSD), alcohol and drug addictions, and personality disorders may also lead to suicide.

As used herein, the term "patient" means a person who has sought or is in need of medical or appropriate treatment and is under the care or would need to be under the care of a physician(s) or health care provider(s), or is in need of treatment.

As used herein, the term "newer antidepressants" is used as that term is understood in the art, and generally refers to antidepressants excluding traditional tricyclic or tetracyclic antidepressants and excluding MAO (permanent inhibitor).

Specifically, the newer group of antidepressants includes, but is not limited to, serotonin reuptake inhibitors, selective norepinephrine reuptake inhibitors (SNRI), combined action SSRI/SNRIs, SARIs (serotonin-2 antagonist/reuptake inhibitors), alpha-2 antagonists plus serotonin-2 and serotonin-3 antagonists, serotonin/norepinephrine/dopamine reuptake inhibitors, norepinephrine and dopamine reuptake inhibitors or other antidepressants. These include but are not limited to fluoxetine (Prozac), norfluoxetine, paroxetine (Paxil), sertraline (Zoloft), fluvoxamine (Luvox), citalopram (Celexa), escitalopram (Lexapro), bupropion (Wellbutrin), nefazodone (Serzone), mirtazapine (Remeron), venlafaxine (Effexor), duloxetine, clomipramine, milnacipran, S33005, reboxetine, nisoxetine, zimelidine, litoxetine, indalpine, gepirone, femoxetine, alaproclate, and racemic forms or derivatives thereof, and pharmaceutically acceptable salt thereof.

Antidepressants also included are:

Serotonegric compounds like 5-HT-1alpha- antagonist (for example NAD-299) and 5-HT-1beta antagonist (for example AR-A2); 5-HT1A receptor agonists and antagonists; 5-HT2 receptor antagonists, Vivalan (viloxazine hydrochloride); AZD4282 (oral glycine); Dehydroepiandosterone (DHEA) with NMDA potentiating effect, or other NMDA receptor antagonists. Other examples of the NMDA receptor antagonists include, but are not limited to, dextromethorphan, dextrorphan, ketamine, amantadine, memantine. Also included are AMPA receptor potentiators, e.g. LY392098; substance P antagonists/neurokinin-1 (NK-1) receptor antagonists, for example, Merk's MK-8 69; Pfizer's CP122,721; nonpeptide Substance P antagonist; Merk's compound A; aprepitant (MK-0 869); or NKP608, L-760735, L-733,060, GR205171; neurokinin 2 antagonists; neurokinin 3 antagonists; corticotropin-releasing factor receptor antagonists like R121919, antiglucocorticoid medications, glucocorticoid receptor antagonists, agents blocking cortisol, e.g., ketoconazole, metyrapone, aminoglutethimide, mifepristone [Mifeprex] (RU486); nitric oxide synthesize inhibitors; inhibitors of phosphodiesterase; enkephalinase inhibitors; GABA-A receptor agonists; agents with neuroprotective effects such as NXY-059, a free radical trapping agent; a typical MAOI's like Selegiline (or transdermal Selegiline); selective MAOI inhibitors like moclobemide, brofaromide, befloxatine, cimoxatone, toloxatone, amiflamine, harmaline derivatives, clorgyline; hormones: in males testosterone; in females estrogen/estradiol; omega-3 fatty acids; other products with antidepressant effects such as folinic acid, leucovorin, tramadol (Ultram); or substances that may enhance 5-HT synthesis and/or antidepressant effects including, but not limited to tryptophan.

As understood herein, the term "a typical antipsychotics" refers to drugs having a higher 5-HT2 affinity and a relative lower D2 affinity as compared with other typical antipsychotic drugs. They also show low EPS compared to typical (conventional) antipsychotics. Atypical antipsychotics include, but are not limited to, clozapine, quetiapine, risperidone, ziprasidone and olanzapine, and Org 5222, melperone, amperozide, iloperidone, SM-9018, JL-13.

The various atypical antipsychotics have a diverse receptor binding profile and they are not only differ from each other but also from the dopamine system stabilizer aripiprazole. (Kane, J. M. 1997, Lawler, C. P. et al 1999, Yokoi, F. et al 2002, Bymaster, F. P. et al 1996, Seeger. T. F. et al 1995, Szewczak, M. et al 1995, Arnt, J. et al 1998.)

As used herein, the term "dopamine system stabilizer" is used as that term is understood by one skilled in the art. Dopamine system stabilizers preserve or enhance dopaminergic neurotransmission where it is low, and reduce it where it is too high. This is accomplished through attaining a balance between presynaptic and postsynaptic D2 receptor stimulation. Dopamine system stabilizers are antipsychotics, but the prototype dopamine system stabilizier, aripiprazole, does not meet the definition of "a typicality" as it does not have a higher 5-HT2 affinity and a relative lower D2 affinity. (See references above on receptor bindings).

Dopamine system stabilizers include, but are not limited to, aripiprazole, preclamol, tolipexole, terguride, roxindole and pharmaceutically acceptable salts thereof. Currently, only aripiprazole is approved for clinical use, and it is the prototype for dopamine system stabilizers.

It should be noted that if an antipsychotic shows a therapeutic effect on depressive or negative symptoms in schizophrenia, this does not mean that it would have an antidepressant effect in non-psychotics. Depression in psychosis (including psychotic depression), and depression in bipolar disorder (where psychosis is often predominant) are different categories from MDD or depression without psychosis. These different diagnostic categories cannot be combined together in an analysis to study the antidepressant effect of any medication. (Ohaeri, J. U. 2000.)

Comparison of typical and a typical antipsychotics in psychotic patients (even at a similar dose) in their relative difference on negative symptoms or mood cannot be sufficient to assume an antidepressant property, and results cannot be extrapolate to patients where psychosis is not present.

The ability of the combination treatment to reduce the risk of suicide may be independent of (or at least not limited to) any action of the antipsychotic medications on mood. The combination of an antidepressant with an antipsychotic, preferably an a typical antipsychotic, is likely to be superior to an augmentation strategy with two antidepressants or to starting treatment with a single high dose antidepressant.

There are other strategies that target a faster onset of antidepressant action, (Montgomery S. A. 1997, Blier, P. et al 1997, Garattini, S. 1997,) and if these were equally effective on reducing the risk of suicide, they may be preferable due to their potentially less severe side effects. Stimulants are known to have fast onset antidepressant action, and are also used in combination for TRD (Ayd, F. et al 1987). Antidepressants with noradrenergic-serotonergic synergism, (either as a single antidepressant possessing these qualities, or as two antidepressants combined) have shown more rapid onset than SSRIs. (Glenberg, A. J. 2000, Quitkin, F. M. et al 2001, Nelson, J. C. et al 1991). Augmentation strategies used for treatment resistant depression could also be considered for initial treatment. However, the rapid onset antidepressant action is unlikely to give the same protection than the antidepressant-antipsychotic combination, and the risk of suicide is still present with the more rapid onset antidepressant strategies. Therefore the antidepressant-antipsychotic combination has a unique role in the prevention of suicide. No other combinations have been used for initial therapy; they are used in treatment resistant depression only.

If typical (or conventional) antipsychotics are used as adjunct to antidepressants a low dose should be given. The doses of the typical antipsychotics are also often given in "chlorpromazine equivalent" doses. (See e.g. conversion charts at DeBattista, C. et al 2003, p91; Jenkins S. C. et al 1990, p134). A low dose of an antipsychotic would mean a chlorpromazine equivalent" dose of 25-50 mg, or up to 100-150 mg q d.

The antidepressant-(low dose) antipsychotic (in particular the a typical antipsychotic or dopamine system stabilizer) combination may also be used for the treatment of "cognitive distortion(s)", when the cognitive distortion(s) lead to functional impairment, or serious health hazard. The consequences may include of clinically significant distress, or impairment in important social, occupational, or other important areas of functioning, or deterioration of health.

The term "cognitive distortion" is used as it is understood in the art (Burns, D. 1980, Beck A, et al 1979, Beck, J. S, 1995, [p119.]), and may include overgeneralization, all or nothing (always-never) thinking, discounting positives or negatives, blaming and "labeling", assumptions and predictions, and emotional reasoning, all of which lead to "jumping to conclusions", without analysis of the facts.

Cognitive distortions may contribute to or worsen a number of illnesses like addictions, smoking, pathological gambling, impulse control disorders, anger, with consequent relationship (marital, work etc) conflicts, major depression, anxiety disorders (e.g., generalized anxiety disorder, panic disorder, OCD, PTSD), personality disorders, obesity, eating disorders (e.g. anorexia nervosa, bulimia nervosa), or possibly even some childhood disorders like oppositional defiant disorder, and conduct disorder.

If the method of the present invention is used for the treatment of cognitive distortions or smoking cessation/nicotine withdrawal, the criteria of the diagnosis of unipolar depression may not need to be present.

If the method is used for obesity/weight gain, or for smoking cessation (where there is also a risk of gaining weight) then an a typical antipsychotic like quetiapine or aripiprazole that is the least likely to increase weight should be chosen (olanzapine would be less preferable or even contraindicated). Similarly antidepressants with side effects of significant weight gain should be avoided.

EXAMPLES

The following examples are intended to illustrate the invention and should not be construed as limiting the invention in any way.

In the first hypothetical case a middle age male patient comes to the Family doctor with vague somatic complaints. Upon examination no physical problems are found, but in response to the doctor's screening questions about mood and depression the diagnosis of MDD is made. No psychosis or delusions are present. There is no history of elevated mood or substance abuse. The patient does not meet criteria for treatment resistant depression, as he is not on any antidepressant. However, two years ago he had been on an antidepressant (fluoxetine 20 mg q.d.) for a year, while he was living in another state. He denies suicidal ideation or plans to the doctor. Family history is positive for depression, and one aunt had committed suicide. Treatment alternatives are discussed with the patient and fluoxetine (20 mg q d) and risperidone (1 mg q d) combination is chosen. The patient is also referred to cognitive therapy. The initial assessment of the therapist reveals that the patient uses significant amount of cognitive distortions (e.g. "all or nothing" [never/always] thinking, self-blaming, "labeling" self and others, predictions). In continuing with the medication combination and therapy the patient makes a progress; his depression lifts and his cognitive distortions diminish in frequency and severity. The patient later reveals in therapy that he was feeling pretty hopeless and angry at his work situation and felt that "nothing else would help his situation than leaving this world". These symptoms (his suicidal thoughts) and his desperate feelings improved within a few days of the medication combination "even before his depression went away".

In the second hypothetical example the patient is presenting herself to the emergency room (ER) after an argument with her family. MDD is diagnosed (without psychosis or delusions). Her 12 year old son is "oppositional, defiant", her teacher husband is jobless for 6 months but does not go to any job interviews. They rarely talk to each other except the arguments. She feels she tried everything to improve her situation but now she wants to kill herself as a way out. She had been put on paroxetine (Paxil) 20 mg q d two weeks ago by her Family doctor without much improvement (yet). Risk/benefits/alternatives are discussed in the ER with the patient, but she is reluctant to take any antipsychotics saying that "she is not crazy or schizophrenic". Upon further education (and strong recommendation by the ER doctor) she is willing to try 50 mg of quetiapine (Seroquel) and actually takes the medication in the ER. It is than prescribed as 50 mg q HS. (There is no agitation present.) She is admitted to the psychiatric department on a voluntary basis. In 24 hours her suicidality vanishes. She admits that she had contemplated suicide for several weeks now, and this was not related to yesterday's family argument. However she is complaining of lightheadedness and continues to express reluctance to take an antipsychotic. After discussion of alternatives and in the light of her improvement (that she is acknowledging), she is willing to switch from quetiapine to a dopamine system stabilizer (aripiprazole 5 mg q HS), and does continue to do well on this. (She understands that this too is an antipsychotic, but the concept of dopamine system stabilizer is more acceptable to her). She also continues to take her paroxetine.

In both of the above patients the antipsychotic is discontinued in two months. Although some patients may show a relapse with the discontinuation of the a typical antipsychotic; the patients in both of these hypothetical cases continue to do well just on the antidepressant at the 10 months follow up. In the first patient the depressive symptoms return and the increase of fluoxetine is providing only temporary relief. At the 12 months follow up he is feeling very depressed again on 50 mg of fluoxetine. Pharmaceutical tolerance to fluoxetine is assumed, and risperidone is restarted at 1 mg q d with dramatic improvement within one week. Two months later this male patient notices galactorhoea (milking of the breast) that is found due to the prolactin elevation from risperidone. Risperidone is discontinued, but within a week his depressive symptoms return. He is than started on 50 mg of quetiapine a day, and does well. Although the patient has a strong family history of recurrent major depression (despite of continuous SSRI intake in these relatives), he continues to do well on fluoxetine-quetiapine combination, and his depressive relapses are avoided at the 5 year follow up.

There may be many variations from the situations shown in these hypothetical examples. As in all treatment, the final decision is always up to the patient and the treating clinician. The continuation of antidepressant-antipsychotic combination beyond the acute phase may also need to be considered especially for the benefits of preventing disease progression (modifying the course of depression), preventing recurrence, preventing delusional/psychotic depression, providing a neuroprotective effect, treat the residual symptoms of depression, preventing the development of tolerance toward the antidepressant (loss of its effectiveness), or preventing the antidepressants paradoxical effect of sensitizing the patients to depression, worsening of depression or relapse.

As in all treatment, the final decision is (always) up to the patient and the treating clinician. Offering to our patients more than one options that include the combination use of psychotropic medications can show many advantages. With this we are involving them in the decision-making, but we are supposed to discuss with them the risks/benefits, side effects of the medications, and available alternatives anyway.

If the patient opts to take only one medication, an antidepressant, let's work with him or her. But if the patient (as usual) is 'tormented' by the depression or depression and anxiety, or has a suicidal ideation, hopelessness, or (after we educate them) expects/wishes an "immediate" improvement [although —like most depressed—still maintaining his/her 'basic beliefs' that "nothing would help anyway"], we should put more weight on the use of medication combination (preferably by adding an atypical neuroleptic or a "dopamine system stabilizer").

In psychiatry we are not afraid of prescribing more than one medications to our patients, and the treatment of depression should not be an exception.

The treatment of depression can be started right away with more than just one medication, the antidepressant.

Predicting which patients will commit suicide is an impossible task, and there are no models of suicide risk assessment that had been empirically tested for reliability and validity. (Simon, R.I., 2002.) It is often difficult for the clinicians to assess the risk of suicide systematically, due to the large volume of the patients, and due to the limited time and resources. The information being available is often limited. There is a continuum in the risk assessment from only asking the patients if they are suicidal, to performing formal systematic suicide risk assessment. It had been admitted even in academic publications that the former is much more common. (Simon, R.I., 2002.) Unfortunately, according to Simon, the "no harm contract" is unreliable, and short hospital length of stay, rapid patient turnover, brief outpatient and partial hospitalization visits, and the split treatment in managed care setting, results in difficulties and that the suicide risk factors are usually not recognized by the clinicians. (Simon, R.I., 2002.) Only the sickest patients are admitted to inpatient psychiatric units, (Simon, R.I., 2002), and the average length of stay (median) for depression/mood disorder can be as little in some (multi-county US) geographical areas as six days. (Mode: 4 days). The length of stay for patients whose medication need to be adjusted may actually be even less, as patients requiring ECT take off from the average hospital days from the former group. (Depression and other mood disorders in Southwestern Pennsylvania). The assessment of suicide is further complicated by the fact that approximately 25% of patients at suicide risk do not admit to being suicidal. (However, in most cases they had communicated suicidal ideation or intent to family members.) (Fawcett cit#18. <also referenced in: Simon, R.I., 2002). Patients, who deny suicide risk, usually do not meet Managed Care criteria for hospitalization.

We have to balance the risk/benefit of our intervention both for the individual patient and for the group of patients we are treating. This had been customary for long, in the medical practice. A good example for this is of how we were treating appendicitis. If the patient showed some typical symptoms that he or she might have appendicitis (specifically if the WBC was also elevated), then the surgeon was operating on. The surgeon had rather operated on healthy people for whom it turned out on the operating table that they did not had an infected appendix, (taking out the appendix anyway), then wait until it became obvious that the appendix had perforated. This is quite a standard procedure that surgeons followed. The risk of dying from the operation (without an infected appendix) was far less compared to waiting and having the (high) risk of death from operating late with a perforated appendix.

The clinicians have a responsibility of not only weighting the risk of the individual but also the risk of a group.

We are following similar procedures and we give thiamin routinely for everybody in the emergency room before giving IV glucose, (therefore preventing Korsakov's syndrome in alcoholics). We are routinely testing for drug screen in the ER (and the patient gets charged for the cost); even when the patient says that he or she is absolutely not taking any illicit drugs. This is a standard procedure and good clinical practice. The risk of being operated on or getting a blood or urine drug screen is not the same. Nevertheless, we take into account the risk/benefit for a group not just for an individual. So why are we not more vigorous in preventing suicide? We are not saying that we should blindfoldedly prescribe a combination of psychotropic medication for every depressed person against their will, but to discuss the risks/benefits and alternatives with the patients as we mentioned it above. It is fortunate, that in this case, with the medication combination we are not only targeting the reduction of suicide (for the individual and for the group as a whole) but other benefits as well, such as a more rapid resolution of the depressive symptoms, the reduction of anxiety, and even a higher response rate (in %) to the treatment. (One could speculate that if using the SSRI-atypical neuroleptic combination would increase the response rate of treatment-resistant depression, then the percentage rate for improvement would be also higher if given for everybody who is clinically depressed, that is without separating the 'responders' from the 'non-responders'. This speculation is probably correct, but by itself would not substantiate the added risk using the neuroleptics. With this rationale, the two step strategy would seem still to be the logical step, to treat the depressed patients with antidepressants first, and reserve other strategies for the treatment-resistant group only. In the argument to consider, or start using the combination treatment right away in all those who are clinically depressed, it is the decrease of suicide rate that is the paramount important factor. The other added benefits from the medication combination like the "immediate" response, the decrease of anxiety, or a higher response rate as for the whole group are only secondary.

It had been noted that in assessing suicide the focus should be on the characteristics of those who commit suicide rather than on the characteristics of patients with suicidal ideation. (Forster P., 1994.) The same article also notes that major depression is associated with the largest number of completed suicide and half or more of all who commit suicide qualify for this diagnosis. About 15% to 20% of all patients with serious affective disorder will kill themselves. (Forster P., 1994.).

On the other hand 8% of borderline personality disorder (BPD) patients will commit suicide. (Forster P., 1994. cit#21.). BPD is a separate diagnostic category from major depressive disorder and not even listed under the mood disorder category (See DSM-IV-TR.). It is also known that in treating borderline personality disorder (BPD), we are using "all of the available psychotropic medications, and combinations of them". (See also Gabard's video Sep. 9, 1992,—and published by APA in 1995, Markovitz, P. J. et al. 1991, U.S. Pat. No. 5,589,512 on BPD filed January 1994,). It is true, depression is only one of the comorbid conditions associated with BPD, some others being rejection sensitivity and cognitive distortions to the extent of "mini psychosis" (See also Gabard's video Sep. 9, 1992,—and published by APA 1995). (For diagnostic criteria please refer to DSM-IV TR.) Our point is that with this disorder we were not afraid of using the combination of antidepressants with antipsychotic medications or even adding a mood stabilizer. Yet in major depressive disorder; in serious affective disorder with 2-2½ times more risk for committed suicide, we continue to refrain from using or even trying this combination. In BPD at times we are even using clozapine (Clozaril) despite for its high risk for agranulocytosis and despite that it had been prohibitively costly, due to the need of weekly or biweekly blood draws (Frankenburg, et al. 1993). We are not recommending Clozaril to treat major depression or other depressive disorders, (see also U.S. Pat. No. 4,310,524 April 1980, on TCA and α-adrenergic receptor blocking agent: clozapine, to achieve rapid onset antidepressant activity. Please note, the antidepressant is TCA, not SSRI, or not of the new generation.), when other much safer (and cheaper) atypical antipsychotic medications are now on the market. However, we do advocate taking a closer look, and considering using the "new generation atypical neuroleptics" or the even newer "dopamine system stabilizers" together with the antidepressants.

What is deceptive at the first look is, that patients with BPD may show more frequent suicidal gestures and may struggle with almost constant suicidal ideation, but the fact remains that the risk of committing suicide is still 2-2½ times more in people with serious affective disorder then in BPD. [For the statistics of suicide risk, please see: (Forster P., 1994.)]

For us in the medical profession it would not be fair to continue hiding under the excuses of the added risk of the potential side effects of the antipsychotic medications, specifically with the availability of some of the safer atypical antipsychotics.

One of the major concern about to use a neuroleptics had been their potential side effects. Although even with the traditional antipsychotics the development of neuroleptic malignant syndrome (with fever, rigidity, and increase in creatine phosphokinase—CPK) had been rare, but this syndrome is potentially lethal. Now that the psychiatrists are more aware of that syndrome they may be able to intervene and start treating it early with better outcomes. In addition and more importantly, the development of neuroleptic malignant syndrome (NMS) may be diminished with atypical antipsychotics. (Caroff, S. N. et al. 2002.).

Another concerning side effect is tardive dyskinesia that has a prevalence among individuals treated with traditional antipsychotics that range from 10% to 15% in young patients, and 12% to 25% in chronic patients. It is has been estimated that up to 90 percent of the cases of tardive dyskinesia goes unrecognized even in academic residency training impatient units. (Rotrosen, J., et al. 1995.). Vitamin E might prevent or reverse this side effect and have prophylactic or therapeutic benefits. (Rotrosen, J., et al: 1995.).

However, the atypical antipsychotic drugs are associated with reduced potential for inducing extrapyramidal symptoms and other movement disorders. Atypical antipsychotics have reduced liability for inducing tardive dyskinesia and show antidyskinetic properties in patients with existing TD. With quetiapine it is reported that the risk of TD was similar to olanzapine and significantly less than haloperidol in all age groups. With olanzapine the annual risk of TD is estimated about $1/12^{th}$ of the risk associated with haloperidol. One year risk of TD of all patients was calculated to be 0.52% with olanzapine and 7.45% with traditional haloperidol. The annual risk of TD with risperidone is ⅙ of the risk of haloperidol or $1/6^{th}$ to $1/10^{th}$ of the conventional drugs. (Caroff, S. N. et al: 2002.). The "dopamine system stabilizers" are expected to have even less adverse effects (Krammer, T.A.M., 2002).

Carroff's article also reports that combining data from many studies indicate that the relative risk of drug-induced acute extrapyramidal symptoms or EPS may be expressed in declining order in the following: the typical antipsychotics (high potency >low potency) >atypical antipsychotics (risperidone >ziprasidone >=olanzapine >quetiapine). [See also ref. for the later for EPS being like with placebo.] This article also states that "There is a fairly consistent and convincing evidence that the atypical antipsychotics have significantly reduced liability for TD and are also effective in suppressing dyskinesia in patients with preexisting TD. In some studies of atypicals the incidence of TD is no greater than the rate of spontaneous dyskinesias among untreated schizophrenic patients." (Caroff, S. N. et al: 2002.).

Although written consent for neuroleptics are not required for outpatient setting, many large institutions adapted such a policy. The side effect profile of a typical antipsychotics is so much less, that in a health system that is a part of a major chain of medical and psychiatric/inpatient and outpatient services, a meeting was held, where the issue of abandoning their written consent form for TD/NMS was seriously considered. (Written communication).

The issue of how long one should take an antidepressant needs to be discussed with the patient. There are only general guidelines for this. The "rule of thumb" varies by how many times the patient relapsed (possibly also taking into account the family history), the patient's age, and (with the newer safe antidepressants) if the patient wants to risk a relapse. These guidelines are known to the clinicians. Since there are no data on starting the treatment of depression right away with the combination of psychotropic medications, no definitive guidance can be given on how long one should continue to take the neuroleptic. The only data we can rely on comes from treating psychotic depression and from the sporadic case reports in the treatment of refractory depression. In some of the case reports when either the patient run out of risperidone over the weekend (Kaplan, M. 2000), or when 3 weeks later it was discontinued (O'Connor, M., et al 1998) the patients anxiety or agitation returned. Again these were treatment-resistant depression. The reinstated medication (neuroleptic) came with an immediate relief. For other patients taking risperidone for 2 weeks or 3 months, the discontinuation of the added neuroleptic did not cause deterioration few weeks later (O'Connor, M., et al 1998). Parker, G., et al. (2002) reports that they have treated treatment-resistant non-psychotic depression, and one of their patients presented in a case report improved with the addition of olanzapine, and worsened when it was tapered off. The same response was observed when the atypical antipsychotic was reinstated, or again tapered. Pitchcot, W., et al. (2001) reports that their patient with a long history of treatment-resistant non-psychotic depression improved moderately on venlafaxine but on 5 mg of added olanzapine experienced a marked improvement with a complete remission. However, when olanzapine was stopped due to it's side effect causing weight gain, the patient experienced a new depressive symptom after 4-5 days. Taking the olanzapine again, the patient experienced a dramatic antidepressant response again, maintaining the full remission for 15 months [continuing with the medication combination].

Since TD is still a concern with the atypical neuroleptics, it is fair to say that we should follow a similar 'rule of thumb' then with beztropine: that is to reassess the patient in a few weeks and again in a few months, and attempt to discontinue it if clinically indicated, and the patient is doing well. If symptoms reoccur, that will shift the clinician's decisional balance to reinstate the neuroleptic. For psychotic depression some recommended using the neuroleptic for one year as the depressive relapse is high otherwise. (Keck, P.E. et al. 2000 (a),). Time and experience with this medication combination will teach us more. The patient's history for suicidality, (suicidal risk factors), impulsivity, 'near-paranoia', comorbid disorders (anxiety, alcohol or substance abuse/dependence, personality disorders), or strong cognitive distortions may also guide the clinician toward continuing with the more vigorous treatment of depression with the combination of psychotropic medications.

In targeting and specifically designing an approach of trying to solve (most/all) of the patient's problems—either pharmacologically and/or with psychotherapy can result in greater success than separate individual strategies alone.

Let's see some other reasons and other rationales for using the combination of antidepressant antipsychotic medications in clinical depression/major depression (non treatment-resistant major depressive disorder).

In a retrospective analysis of suicide committers with major depression showed that many of them have received inadequate treatment. (Forster P., 1994.) So if the effectiveness of the antidepressant treatment could be increased in any way, it would be logical that the suicide rates would decrease. Actually, this had already been proven (Rihmer, Z. 2001). Furthermore it had been shown that among the depressed patients who committed suicide many of them actually had psychotic depression that went unrecognized so they were not receiving antipsychotic medications. (Forster P., 1994.) Therefore the adjunctive use of antipsychotic medications could not only enhance the effectiveness of the treatment of depression, but it would also provide a safeguard in case of unrecognized psychotic depression, and therefore again prevent suicide. (It had been estimated that a significant proportion, 15% of major depressive episodes fulfill the criteria for psychotic subtype. (Gumnick, J.F. et al. 2000).

In addition, if we were using adjunct antipsychotic medications for the treatment of clinical depression, the overall improvement—as for the group, would also be expected to improve. Nierenberg had noted that in many cases, the cause of treatment-resistant depression may be an unrecognized psychosis. (Nierenberg. A. A., 1992). (That may explain it again—at least in part—of why did the "treatment-resistant" depression group improve with the addition of an antipsychotic medication.)

Cognitive distortions like jumping into conclusions without the analysis of the facts; prematurely getting into conclusions, are characteristic for depression. Cognitive therapy specifically addresses this issue by teaching patients of how to recognize and correct these distortions. Others, (Yapko tape) call cognitive distortions as "global thinking", and report that it is the thinking style of the depressed. It seems however, that there is an overlap between the cognitive distortions; the "mini psychosis" of BPD; and the "full blown psychosis" of psychotics; all of them being out of touch with reality but in different degrees.

We psychiatrists also know that antipsychotics are not particularly effective in chronic delusions with only one delusional idea (monoideatic delusions), nevertheless we are prescribing them despite of its limited usefulness. (The neuroplasticity model for chronic delusion may explain its relative resistance to medications [Spitzer M. 1999]). Now, that we postulate that the atypical antipsychotics may be useful for depression, we may wonder if in fact these medications are—in part—targeting the cognitive distortions that overlap with psychosis. In fact it may be worthwhile considering to reclassify depression as a "thought disorder", or at least to note that the overlap between depression (mood disorders), and "thought disorders" is not constricted to psychosis or psychotic depression per se. [For those less familiar with the field of psychiatry, disorders like psychosis, schizophrenia, delusional disorders are listed under the category of "thought disorders, and are treated by antipsychotic medications. Depression—with the exception of psychotic depression—was not (and is still not) considered a "thought disorder. However, the particularly strong cognitive distortions in depressed, through the impaired reality testing, in our opinion do overlap with psychosis. In addition, it had been shown, that antipsychotics do show some antidepressive action, so they may be useful in the treatment of depression. All these points to the direction to view depression—at least in part—as a thought disorder]. With this, the use of antipsychotic-antidepressant combination for the treatment of depression gets further supported.

Cognitive distortions also play a role in anger attacks that 30-40% of depressed patients display. (Koh, K. B. et al. 2002). A significant association between depression and violent behavior in community samples also had been established. (Koh, K. B. et al. 2002). Some reports 28-44% of violent behavior in depressed outpatients. (Hughes, D. H. 1998). Antipsychotics had been used to reduce violence in acute settings, like in ER (Currier, G. W., 2000), and also with psychotic/bipolar patients in long term use. It is also used for 'pathologic aggression' (Collaborative Working Group on Clinical Trial Evaluations 1998 c). Therefore it is questioned again, why don't we use them as adjunct medication in the treatment of depression (major depressive disorder, dysthymia, "double depression". . . )?

It can be speculated that jumping to conclusions without analyzing the facts may lead to impulsivity and may increase the chance for suicide. In fact it is known that impaired reality testing as shown in alcoholism and drug abuse, is associated with significantly increased risk for suicide. Alcohol is associated with 25 to 50% of all suicide and is the second most comorbid factor after depression. (Forster P., 1994.). Therefore addressing cognitive distortions, and/or the source of impulsivity is essential.

Depressed patients (with their strong cognitive distortions) may not only misperceive information coming from the environment (like miscommunications in their relationships leading to social isolation), but also misperceive stimuli coming from their own body (Szadoczky, E. 2001). In fact increased somatic symptoms are noted in the depressed, (Stahl, S. M. 2002, Kirmayer, L. J. 2001, Kirmayer, L. J., et al. 1993, Szadoczky, E. 2001,), and the majority of the depressed patients present with only physical symptoms to primary care providers (Pincus, H.A. 2001,). This also points out, that part of the problem is with the perceptual disturbance—a symptom, in which just like for delusions it would be logical to use neuroleptics in combination of the antidepressants). [The use of antidepressants in chronic pain and in some somatic problems had been recognized before. (Lynch, M. E., 2001, Bilier, P., et al. 2001, Gruber, A. J., et al. 1996,)].

It would be important to reassess the role of cognitive distortions in hopelessness and suicide. A study by Fawcet (as referenced in: cit#16 in Forster P., 1994.), confirmed the predictive value of hopelessness in suicide, and that hopelessness is the greatest predictor of suicide risk beyond the first year. However suicide occurs in only 5% of terminally ill patients and their greatest risk factor is untreated depression (Forster P. 1994.). Therefore it is not hopelessness per se, but its perception—that is the cognitive distortion characteristic of depression that seems to be the most important factor. (For strong perceptual disturbances [e.g. hallucinations,] we had been using antipsychotics.). The adjunctive use of antipsychotics with SSRIs and newer antidepressants in the treatment of depression (major depressive disorders and the like) is again supported by this argument.

Rumination often seen in the depressed, (e.g. excessive guilt, self-blame, low self-esteem) may overlap with cognitive distortions and also with obsessive-compulsive disorder (OCD). In fact, depression can be viewed that the patients cannot let go of mainly focusing on the negatives. They do ruminate on the negative life events. It is notable, that the adjunct use of antidepressant-antipsychotics was useful in the treatment resistant OCD. (Mohr, N. et al.:2002, Atmaca, M. et al.: 2002). Therefore this medication combination targets another depressive symptom, and substantiates its use for depression, and the decrease of suicide.

Social withdrawal (and lack of social support) had been also mentioned as a risk factor for suicide. Social withdrawal or lack of social support is found almost half of suicides (Forster P., 1994. [cit#261). We know that atypical neuroleptics (atypical antipsychotics) improve the "negative symptoms" including social withdrawal, at least in psychotic patients. (Purdon, S.E. et al. 2001, Berman, I., et al 1999, Keefe, R.S.E., et al. 1999,). Therefore the use of adjunct atypical antipsychotics or "dopamine system stabilizers" in clinical (non-treatment-resistant) depression would be supported by this logic as well.

Additionally, it is known (separate from all other rational that we list here) that antipsychotic medications, atypical neuroleptics have a positive effect on improving depression in psychotic (schizophrenic) patients. They also reduce hostility and the risk of suicide in this patient population. (Keck, P. E. J. et al. 2000 (b), Collaborative Working Group on Clinical Trial Evaluations, 1998 b,). In fact in an analysis extending to 1 year, in psychotic patients the annual suicide attempt rate with atypical antipsychotics showed a 2.3 fold reduction compared to patients receiving haloperidol, an older antipsychotic. (Glazer, W. M. 1998, also referenced in Keck, P. E. J. et al. 2000 (b),).

We also know that suicidal individuals often find their thoughts constricted to a narrow range of topics and that they tend to constrain their options prematurely. (Forster P., 1994.) In other words this is cognitive impairment and cognitive distortions. Again, the atypical antipsychotic medications had been found to have beneficial effect on cognitive impairment, as measured by psychological testing (at least in psychotic patients). (Purdon, S.E. et al. 2001, Berman, I., et al 1999, Collaborative Working Group on Clinical Trial Evaluations, 1998 a,). That would be an additional support for the adjunctive use of antipsychotic medications with antidepressants in unipolar, non-treatment-resistant depression.

Some articles also identify the so-called suicidal depressive syndrome (not listed under DSM-IV TR) that patients with major depression at highest risk generally also have feelings of worthlessness, anxiety, depressive delusions and more sleep disturbances. (Forster P., 1994. cit#6). Anxiety itself is a unique and short-term risk factor for suicide, and in patients with major depression, anxiety predicted 93% of suicide within one year of assessment. (Forster P., 1994. cit#5=Fawset). Patients at highest risk for suicide are those with more severe anxiety combined to depression. (Forster P., 1994. cit#17). Therefore, again, the addition of a neuroleptic as it has an anxiolytic property would be justified.

The co-occurrence of anxiety and depression is particularly interesting from the standpoint of our analysis.

In their original article treating resistant major depression with olanzapine and fluoxetine the authors (Shelton) did not find a statistically significant improvement in depression with the Hamilton rating scale for depression, but they did find it with the Montgomery-Asberg depression rating scale (Shelton, C. R., et al. 2001 (a).). Nevertheless, the author had find their finding, the improvement of depression, clinically significant. (Written communication from Shelton.)

In our explanation, what might have gone unrecognized by these authors (and others in the process of replicating the study) is, that there is a specific, significant difference between these two psychological rating scales. Namely, the Montgomery-Asberg depression rating scale puts a relatively higher emphasis on anxiety (1 in 10), while the Hamilton rating scale for depression has about the ratio of rating psychic anxiety 1 in 21. [Somatic symptoms/anxiety are measured separately.]In addition, the Montgomery-Asberg depression rating scale allows a 0 to 6 measurement of the inner tension, potentially allowing more emphasis in the statistical analysis. In comparison, the Hamilton depression rating scale there is a 0-2, 0-3, and for anxiety 0-4 scoring. (For replicative studies, it is important of not to use a "simplified" Hamilton rating scale, where there is only a checkmark for the depressive symptoms, not allowing any severity rating: [(See references for the scales: (Stajatovic, M. et al. (eds): 1999.)]. That would make the Hamilton scale even more 'insensitive' to changes in anxiety. Never the less, what the authors (Shelton) might have actually measured (in coming up with a statistical difference in one scale, but not the other), was the relative improvement in anxiety. It is known that antipsychotics reduce anxiety. [Although this group of medications had been named "major tranquilizers" early on, it was because of their strange quietness or blandness (ataraxia) that the patients were displayed. (Van Kammen, D. P. 1995).]Undoubtedly, other factors might also play a role in why the combination of antidepressant with atypical antipsychotic medication results in an improvement in the treatment-resistant depression. We have already reviewed above some of the key factors that in our interpretation can contribute to the improvement of depression by adding an atypical neuroleptic, or a "dopamine system stabilizer".

In finding a rational, that why would the addition of a neuroleptic result in an almost immediate positive response in depression; we have to also rely on a psychological explanation. In short an immediate improvement in any of the patient's symptom would be a direct reinforcement that change is possible, and that would change the patient's expectation. Depressed patients, in general, have a low motivation, a decreased energy and interest, and an expectation that 'why bother', nothing is going to change, nothing is going to help. They have a helplessness and hopelessness. In fact these symptoms are characteristic of depression (and also a significant risk factor for suicide) [for helplessness being an increased risk for suicide see reference : A study by Fawcet (cit#16 in Forster P., 1994.)]. Unfortunately, this is why many depressed people don't seek treatment. It's ironic, that when they come for an evaluation to their doctor, this negative expectation is just being reinforced. They cannot get an immediate relief, the evaluating doctor is asking a lot of questions about painful or negative aspects of their lives, (at times it seems to them that he/she is just dwelling on their problems). At the end of the first visit they are told that the antidepressant cannot help for several weeks. As a result the negative expectation is reinforced, and due to their hopelessness, they may discontinue taking their medication. (see also Yapko tape). In fact nonadherence to the prescribed medication can account for as many as 20% of the cases considered to be treatment-resistant. (Thase, M.: 2002 (b), references >Cit.#11.) About 24% of patients do not inform their physicians that they stopped taking antidepressants. (Demyttenaere, K. et al. 2001). Other publication reports that in primary care, more than one third of patients fail to refill their initial (antidepressant) prescription, and nearly half discontinue it within three months. (Pincus, H. A., et al. 2001,).

Therefore addressing and relieving the anxiety—which is present as a comorbid disorder in 56.8% of patients with known non-bipolar, major depressive disorder (Zimmerman, 2002) would result in a drastic change in the patients' expectation. Since a positive change had occurred (a relieve in their anxiety, an improvement in their overall feelings), they would show more hope. Therefore, by pharmacologically addressing one symptom, improvement in other related symptoms, and in general in the depression as whole, can be expected. That would explain the "immediate" improvement from the psychological point of view.

Sleep disturbances (insomnia) is one of the depressive symptoms often present. So, addressing this problem early on would result (similarly) in improved compliance and in a more immediate improvement in the overall depressive symptoms as well. (Temporarily adding a sleeping pill like zolpidem (Ambien), till the depressive symptoms, and with them, the complaint of insomnia would lift can therefore have a more beneficial effect then what we realize, i.e. the improvement of sleep per se.)

It is important to note, that neuroleptics, in particular atypicals may improve sleep. (Salin-Pascual, R. J. et al. 1999.) That may again point to a benefit of the combination use of these medications with the antidepressants. (See also Eli Lilly patent # WO 99/61027 SSRI-antipsychotic combination use for adverse events associated (with SSRI administration] with the treatment of major depression, partial, or treatment resistant depression.)

The more symptoms we address and correct "right away", the better the chances of patient satisfaction and global improvement. While I was in training, I have heard stories of the "miracle" effect of using stimulants as antidepressant in some medically ill/elderly patients. (Kamholz, B. A., et al. 1996). (See also reference for stimulant use in medically ill/elderly: Satel, S. L. et al 1988; also referenced in: Willner, P. 1997,) I have never put it in this context up till now, but a similar explanation may play a role here that by improving the patients' energy we see a quicker response then with other antidepressants. With the global improvement, the patients' expectation changes too, and hopelessness gets less pronounced, or goes away.

(However in defense of biological explanations, we have to note also the following: High placebo response plays a role in the treatment of depression (mean placebo response rate for major depressive disorder is about 30-40% with some studies reporting rates of 70% [Schatzberg A. F, et al 2000,]. Some also suggested with studies supporting that trend, that patients with more severe depression respond well to antidepressants whereas those mildly ill respond equally well to antidepressants and placebo. (Khan, A., et al. 2002, [see also Rush, A. J., 2000, Thase, M. E. 2002 a, 2002 c, and Kirsch, I. 2000, on if the drug and placebo effects are additive.); However, it is unlikely that placebo response would be the only explanation here. First, here the (adjunct) medication is chosen specifically to target pharmacologically a specific symptom (the anxiety, cognitive distortions "overlapping" with psychosis; low energy or sleep disturbance respectively), so it is not a "placebo". Second, as we can see in the case report with the risperidone-SSRI combination for treatment-resistant depression (O'Connor, M., et al 1998) —at least in one case —it was reported that the patient did relapse despite the resolution of sleep problem (and despite the additional adjunctive use of a benzodiazepine as an anxiolytic); and it did not gave the same result in the improvement of depression as the added atypical antipsychotic did. So psychological explanation on the role of changing expectations is extremely important, but it is not the full answer.)

We have mentioned above, that the atypical antipsychotic medications (at least in psychotic patients) show beneficial effect on the "negative symptoms" (Purdon, S. E. et al. 2001, Berman, I., et al 1999, Keefe, R. S. E., et al. 1999,). Within the "negative symptoms" the following terms are included: affect blunting which may correlate to such symptoms in depression as decreased interest, concentration, and psychomotor retardation. The term anemia correlates with the symptom of decreased energy. Alogia if due to depression may be because of decreased interest, psychomotor retardation, or decreased energy. Social withdrawal may occur for many reasons, but decreased interest, concentration, psychomotor retardation, guilt, and hopelessness (which are all symptoms of depression) can also play a role. The above is another reason of why the atypical neuroleptics could provide a benefit in the treatment of depression—as adjunct to the antidepressants.

Obviously when both psychosis and depression are present like in schizoaffective disorders, psychotic depression, or even at times in bipolar disorder, both groups of medication are indicated and used, targeting the depressive or psychotic symptoms respectively. (About $2/3^{rd}$ of patients with bipolar (manic-depressive) disorder are having a history of at least one psychotic symptom. Bipolar patients who are psychotic during one episode of affective illness are highly likely to be psychotic during subsequent episodes. [Tsai, SY. M., et al. 2002.]). Antipsychotic medications also showed a value during the manic phase of the bipolar disorder. (See Miller, D. S. et al, 2001, Yatham, L.N. 2002, Sajatovic, M. et al. 2001.). It has been also shown, that about 15% of major depressive disorders, usually those with melancholic features, develop into delusional (psychotic) depressions. (Akiskal, H. S. page 1137, 1995).

In reviewing the recent paper (O'Connor, M. 1998) about the use of risperidone for treatment-resistant depression, it is notable that all of their patients had shown a comorbid anxiety.

For the different type of antidepressant actions see Thase (2000).

The interest in psychopharmacology research is also shifting. Instead of searching for medications with high affinity for D2 receptor, or agents that strongly binds to dopamine receptor, researchers are reevaluating their strategies. Agents can be both agonists and antagonists, or transiently binding to dopamine receptors, having mild effect similar to dopamine but less intense. The newest generation of atypical antipsychotics better named as "dopamine system stabilizers" are exemplified with the prototype of aripiprazole. (Krammer, T.A.M., 2002). It was shown that the single most powerful predictor of atypicality is fast dissociation from the D2 receptor. (Kapur, S., et al 2001). (See also for additional reference Stahl, S. M., 2001 a, 20001 b,). Therefore, quetiapine, with it's fast dissociation from the dopamine receptor—relative to risperidone and olanzapine—may be reclassified in the future as a "dopamine system stabilizer" from it's current group of "atypical antipsychotics". The above may give a better insight in looking at the role of dopamine in the treatment of depression.

We should also keep in mind that the role of dopamine may be specific to a particular brain area. In addition, the different subtypes of receptors mediate different actions, and these are further affected by other neuromodulators. The end result is complex. That may also suggest to look for a molecular/biological solution elsewhere. We know that dopamine (DA) plays an important role in neuronal plasticity. (Spitzer, M. 1999). In looking the global picture, that is the role of neuronal plasticity in depression, the psychological and biological explanations blend together.

Although some may use the terms synaptic plasticity or neuroplasticity as synonymous, it may be better to separate the two phenomena. Synaptic plasticity as it relates to depression (and learning), is primarily referring to changes in the cellular, synaptic and molecular levels, with the focus on glutamate neurotransmission and NMDA receptors. One of the primary interests is on the volume loss of the hippocampus, with possible neuron loss during depression. It had been questioned if stress and elevated glucocorticoid levels (through oxygen radicals and "programmed cell death") may cause hippocampal neuron loss associated with subtypes of chronic depression. (Lee, A. L. et al, 2002; Duman, R. S. et al. 1999,). There is evidence that stress will cause a regression of dendritic process in hippocampal neurons producing loss of neuronal volume, this however, has been shown to be reversible with the cessation of stress. (Lee, A. L. et al, 2002,). There had been an expectation that pharmacological inhibition of NMDA receptors would be protective against insults (and "programmed cell death") (Lee, A. L. et al, 2002,), and that NMDA receptor antagonists act as antidepressants in certain animal models of depression. (Willner, P., 1997,). In frontal cortices of human suicide victims the alterations of NMDA subtype of glutamate receptor had been shown, (Nowak, G., et al. 1995, also referenced in: Heresco-Levy, U., et al 1998, and Krystal, J. H. et al. 1999,). It had been hypothesized that a final common pathway of antidepressant action may be associated with the NMDA receptor complex, as antidepressants may induce adaptive changes in the glycine (GLY) regulatory sites of the NMDA receptor. Antidepressants from every class produced a 2-4 fold reduction in the GLY to inhibit 5,7-DCKA binding to the NMDA receptor-associated GLY sites. (referenced in Heresco-Levy, U., et al 1998,). An antibiotic that had been used to treat tuberculosis, DCS (Seromycine) with a partial agonist character at the GLY site and with an NMDA antagonist-like effect (or mixed agonist/antagonist effect) had been shown to display prompt antidepressant effects (before the X-ray changes), while GLY too had shown an antidepressant effect (reducing negative schizophrenic symptoms). (Heresco-Levy, U., et al 1998,). Others also noted that there had been evidence demonstrating that mood stabilizers and antidepressants exert effects on signaling pathways which regulate synaptic plasticity and cell survival, (Manji/editorial, 2002,).

Unfortunately, there are also conflicting reports that makes the role of NMDA receptor difficult to understand. How can one explain the fact that a competitive NMDA receptor antagonist, a non-competitive NMDA antagonist, and a partial agonist all have shown efficacy in animal models of depression? (Belsham, B. 2001,). In addition the NMDA receptor antagonist (CPP) impairs learning and memory, and the same receptor complex is thought also to be involved in a variety of other psychiatric illnesses. (Shapiro, M., 2001,).

However, it is of particular interest to us, that the glutamate transmission (in patients with schizophrenia) is affected by atypical antipsychotics. (Evins, A.E. et al 1997, as referenced in Scheepers, F. E. et al. 2002,). In contrast to this above study, in cerebrospinal fluid (CSF) no significant change in glutamate concentrations was found after treatment with olanzapine (again in patients with schizophrenia). The authors also note that it is possible that the brain glutamate concentrations are not reflected in CSF. (Scheepers, F. E. et al. 2002,).

The synaptic plasticity model of depression also overlaps with the theory on the failure of neurogenesis (lack of brain cell growth) linked to depression. (Vogel, G. 2000). Neuroimaging techniques show smaller hippocampi in depressed patients, and antidepressant drugs and electroconvulsive therapy (in animals) show significantly more newly divided cells in the hippocampus. This is an addition to the recent discovery that had shown that the brain keeps producing new neurons into adulthood. (Vogel, G. 2000, Duman, R. S., et al 2000,).

Looking beyond the changes in the hippocampus and receptor level in depressed patients, it would be worthwhile to separate the term synaptic plasticity from neuronal plasticity.

Neuronal plasticity, the capacity of the brain to respond to changes (Spitzer, M. 1999,) had been extensively studied in some other conditions where the cortical representations of somatic perceptions can be mapped. (As the brain has no sense of pain, neurosurgeons could operate on patients while they were conscious [in local anesthesia or "woken up" after their sculls were opened] for example to remove a tumor, but to preserve brain areas that are essential to speech, vision or movement. During such operations it was discovered that part of the cortex that is responsible for processing touch sensations and is representing the different areas of the body, has a map-like structure, called "homunculus" in the cortex. Not only touching, but all senses are represented in topographical cortical maps. [See also: Spitzer, M. 1999,]). What is the most intriguing is, that these cortical maps or cortical representations are not fixed, but have the ability to change if the input is changing (i.e. to show neuroplasticity). In a congenital malformation called syndactyly, the fingers are attached to each other (like in a fetal webbing). After the fingers are surgically separated, the borders between their cortical representations emerge in one week. (Mogliner et al. as referenced in Spitzer, M. 1999,). The opposite was also shown in animal experiments sawing the fingers together. Changes in cortical representation do follow this procedure. In a different experiment (seen at PBS), a human volunteer was blindfolded for about two weeks, and it was found through a non- or minimally invasive procedure, that other brain areas started to "took over" the now unused visual cortex, and the cortical representations of the fingertips (touching) had increased. It is interesting to compare that while it takes weeks for the antidepressants to start working, it also took week(s) to see neuroplasticity changes in the above experiments. For a more complex adaptation neuronal changes may take even a year (e.g. cochlea implant). (Spitzer, M. 1999,).

The above experiments are looking beyond the changes in the hippocampus (and are not constricted to the receptor level). Different emotions, or the changes in depressive disorders are not limited to the hippocampus, and other brain areas are also involved.

Beyond the cellular changes in the hippocampus, and beyond the explanation of changes at intracellular level, the only strong support for the neuronal plasticity of depression, that we have seen was the argument that the therapeutic action of antidepressants requires weeks, even though these medications block the reuptake or metabolism of norepinephrine (NE) and serotonin (5-HT) much more rapidly. The conclusion was that therefore the treatment of depression involves adaptation or plasticity of neural systems. (Duman, R. S. et al, 1999,).

Yet it would be interesting to see a synthesis of clinical findings, supporting the neuronal plasticity model of depression from the clinical standpoint. Below we will present our viewpoint that brings the psychological and biological explanations together, and provides further understanding of depression. [These were never presented in this context before].

First we'd like to start with the "domino metaphor" (or "practice makes a master" metaphor). Although traditionally it was believed, that if stroke victims did not regain the function of their arm within a few months, then it was little hope for recovery, we know it now that this is no longer true. Supported by clinical data and not just animal experiments, we know that persons with stroke "learn" of not to try using their paralyzed arms or legs, and as times goes on this becomes an increasingly powerful conditioned response. However, by placing a restraint (a large stuffed mitt) on the patient's functioning arm, he/she is forced to overcome the tendency of not using his/her weaker arm. With physical therapy they are coached 6 hours a day to practice and improve the movements of their weak extremity. They are given tasks like turning dominos over (and cheered for their success). With practice and repetition comes a dramatic change within a few weeks. This phenomenon had been explained as a result of "an increased recruitment of neurons surrounding the area of the primary damage caused by a stroke". The neurons that haven't been killed by the stroke, but are in the vicinity of the damage are sending out connections with other neurons. (Restak, R. M., 2001 and corresponding PBS video). This is the neuronal plasticity that we have also seen in other examples above. In principles we see a similar phenomenon when children's good eye is covered to force the weaker eye to "learn to see". With practice we are relying on neuronal plasticity in a therapeutic way.

Now, if this true on other areas, why wouldn't it be true for depression, or for the treatment of depression? In fact we have unpublicized data available to support that most likely the same is true for depression. Depressed people tend to focus on the negatives, and tend to ignore seeing the positives. Cognitive therapy teaches us to do similar repetitions, that is, to catch ourselves that we have (negative) automatic thoughts, and make necessary corrections by doing an analysis of the facts on both the negative and the positive side. This is the practice that is similar to the "repetitions of the movements" seen in stroke victims above. We just do not have a good visible "mitt" that would force us doing this practice. However medications do help exactly in that direction: We have mentioned above, that the problem in depression is rumination, the repetition and overt focus on the negatives, with cognitive distortion. Actually SSRIs used for treating depression are also working to reduce OCD symptoms, "the rumination". We suggested above that neuroleptics may also be helpful in many ways, and are expected to help decreasing cognitive distortions, that are so characteristic of and contribute to the depression.

However, let see how some experiments from decades ago can be applied in this context, so that with our current knowledge they would clinically support the neuroplasticity model of depression.

One of the experiments, (Haney, C., et al. 1973, also referenced in Yardley, K. M. (1982 b), and see also as related reference: Yardley, K. M. (1982 a),), although was not designed to do anything with depression, but has a great relevance to it, as it shows the importance of how detrimental can a 'negative practice' be even in "as-if" (or role play) situations. In a Stanford experiment they recruited normal healthy volunteers who agreed to take part of a "prison simulation experiment" for up to two weeks. They randomly assigned them to be either "prisoners" or "guards". Unlike the guards, who had some minimal warm-up to the as-if event, 'the prisoners were covertly inducted, without their conscious cooperation. For the sake of "realism", they were arrested in the early morning, on false burglary charges, by actual members of the city police who were cooperating with the experimenters. The prisoners were then subjected to police interrogation and taken blindfolded to the simulated prison.' (Haney, C., et al. 1973, also referenced in Yardley, K. M. (1982 b),). The "prisoners" were further subjected to humiliating and frustrating experiences (and their queries to the police if this had to do anything with the experiment were ignored). After a week the experiment needed to be prematurely terminated, "due to the ensuing emotional disturbances amongst the participants, particularly amongst the prisoners". (Yardley, K. M. (1982 b),). The "prisoners" were feeling powerless, loss of control to the point of oppression, frustration, 'emasculation', anonymity, and arbitrary rule. The later in this case is really resulted in "learned helplessness" that we know as an important causative factor in the development of depression. While this experiment from the early 1970's looks cruel, and we can all hope that this kind of "experiments" can no longer be done today, they show something, that artificially practicing and focusing on the negatives, or be forced to focus on the negatives even in an "as-if" experiment would result in an unwanted emotional disturbance. This is exactly the opposite of what we therapists and health care professionals want to achieve, and an example that "neuroplasticity" works both ways. In a commentary on the above 'experiment' Yardley notes that the outcome would have been different if the participants would have been brought out of the as-if situation every few hours or so to remind them of the as-if framing. (Yardley, K. M. (1982 b),). That means of shifting the balance between the negatives and positives. This is what depression therapy is all about when we give the patients the tools of doing this.

In another experiment unemployed actors were recruited for a depression study. They were paid volunteers, and were asked to act and think as-if depressed, to walk slowly with a bended posture, and think that they are no good, etc. In two weeks they have shown biochemical and other signs of depression, and the actors reported that they had difficulty snapping out of the depression after the experiment was over.

All of the above supports not only the "clinical neuroplasticity model of depression", but also the importance of practice to overcome depression. In this context this is very similar to the therapy of the stroke victims mentioned above. This "domino metaphor" (or "practice makes a master" metaphor) can also be used clinically to motivate and educate patients about depression, and depression treatment.

The above—the neuronal plasticity model—can also give an insight to the course of depression, and to the 'natural' tendency to relapse, of why is that so easy to relapse, if one stops the medication(s), or stops the 'positive "domino" practice'. It was shown, that practicing cognitive therapy can be protective of the depressive relapse, and this is supportive of this view. It was also shown that the combination of antidepressant and cognitive therapy is superior to either treatment alone. [see Thase].

One of the reasons for why the neuroplasticity model of depression is still lagging behind the other observations on the brain's power to adapt is that our technology did not allow us to "map" the cortical representations and changes that occur with the depression. Our brain imaging techniques are improving (George, M. S. 1994, Ketter, T. A., et al. 1994, George, M. S., et al. 1994, Rubin, E., et al. 1994,), but there is another way to assess and "map" changes in the brain. The cortical representation of one's "inner world" may be also reflected by one's vocabulary. It had been shown, that in children, at an early age, words referring to the imaginary world (like fairies, dragons, etc.) shows a relative high ratio to reality based words in comparison to adulthood. (Deme, L. personal communication, Deme, L. 1975,). This "mapping" of children's vocabulary is in turn is also correlates with the finding that children has a greater involvement in fantasy, and have a higher hypnotic susceptibility. (Migaly, P. 1991). Although it is not the same, but assessing patients depression (or feelings) with a psychological test, that we propose for a more accurate assessment of depression, can serve as a "mapping" tool. (See text later and Appendix B and C of the provisional). With an analogy it is like the vocabulary in the RAM or the hardware of speech recognition software. The words used (thought/ruminated) more often are stored upfront (RAM), but other words are still recognized that are stored in the hardware. So mapping of the neuroplasticity changes occurring during or in the recovery of depression is also possible with a psychological tool relying on the vocabulary. (One has to be careful though to balance the testing with counseling and of not to alter with too frequent testing the "positive domino practice" encountered in therapy, or by the positive effect of the medications).

In helping someone to come out of depression (and one's inner world of focusing on the negatives), it had been shown that physical exercise has a value, and an antidepressant effect. (Russo-Neustadt, A., et al 1999, Blumenthal, J. A., et al 1999,). We also know, that in chronic pain, that frequently also overlaps with depression, physical activity has a beneficial effect. Moreover, physical exercise was also shown to be of value in connection with learning and neuronal plasticity. These similarities are intriguing.

It had been questioned before that if for the depressed patients everything would go exactly their way for a few solid weeks, without disappointments, rejections or criticism while everybody would love them, would their depression go away? (O'Connor, R. 2001 p23). Well, it depends. These circumstances could definitely make everybody's life easier, but recovery to a large extent depends on "the domino metaphor" practice above. (However, the "optimal circumstances" raised in the above question are so important that in our upcoming book we are paying attention to on how to achieve the most and get a harmony, a 'full life' not just recovery from depression.) In fact the closing remarks in a book where there is a lot of discussion about neuronal plasticity emphasises that we all should "watch our mental diet". (Spitzer, M. 1999,). In this the author means that we should watch the input we receive (e.g. through violent movies, discouraging news from within the society).

In summary for this section in looking the global picture, that is the role of neuronal plasticity in depression, the psychological and biological explanations indeed do blend together.

A new research of data (although pertaining to a different group of disorders, the bipolar disorder, and bipolar depression) brings up the issue of "neuroprotection" from the standpoint of the neuroplasticity, and "programmed cell death" that is associated with bipolar disorder, and bipolar depression. (Lee, A. L. et al, 2002, Manji/editorial, 2002, Chuang, D-M., et al. 2002, Bown, C. D. et al. 2002, Li, X. et al, 2002,) (See also Spitzer, M., 1999, Grigsby, J. et al. 2000, Fazeli, M. S. et al 1996, Restak, R. 2001, Duman, R. S. et al. 1999, ref. for neuroplasticity). If this data also can be replicated for major depression, there would be an additional benefit at the molecular and cellular level for the combined use of mood stabilizers. [It would be also interesting to see if antidepressants and neuroleptics show this "neuroprotective effect". Some of the atypical neuroleptics had also shown a "mood stabilizing" effect in mania. However, not all mood stabilizers had shown a "neuroprotective effect".]We are getting now mood stabilizers that have substantially less side effects. For now the combined use of a mod stabilizer together with a (newer) antidepressants/or SSRI with or without the added neuroleptic should be considered very carefully only for selected patients when used in non-treatment resistant cases until we get more data, or mood stabilizers with safer side effect profile. In other words their risk/benefit ratio has to be measured before use. [We mentioned for example suicidality or impulsiveness.] However, these medications in combination should be considered to be given right away, to reduce the risk of suicide.

The invention also provides a method where other medications traditionally used for as adjunct medications reserved for treatment-resistant depression, can be considered to be given right away in the treatment of major depressive disorder, other depressive disorders, and/or in disorders high risk for suicide to achieve a reduction of suicide. (See Nelson e.g. for reviewing agents used for augmentation strategies for treatment-resistant depression).

The above claims should not be limited by the patient taking other medications as well, or by using other augmentation strategy by e.g. by combining more than one antidepressants, or by using other strategy like of pushing up the dose of the antidepressant aggressively. This later is usually not followed, unless there is a comorbid disorder (like an eating disorder) where usually higher dose of the antidepressant is required for adequate treatment. Alternatively combining antidepressants and 5-HT agent (like pindolol), with or without antipsychotics should also not limit the above claims. Similarly, addressing sleeping problems right away is important in achieving a rapid response/increased compliance, and should get a weighted emphasis. However, its benefit seems not to be the same as with the psychotropic combination we had been suggesting above.

An antipsychotic medication or a "dopamine system stabilizer" alone and/or in combination with an antidepressant can also be used in other circumstances where depressive symptoms and/or anxiety/irritation could be the predominant symptom in the patients, but the patients/clients do not need to meet diagnostic criteria for major depressive disorder. In this case the antipsychotic medication or the "dopamine system stabilizer" and/or the combination use do not need to be for the reduction of suicide, but for the reduction of anxiety/irritation, and/or the depressive symptoms, and/or compulsivity and/or possibly the reduction of cognitive distortions as well.

Akiskal, H. S. Mood disorders: Clinical features. Page 1137. In: Kaplan, H. I. et al. (eds) Comprehensive textbook of psychiatry. Williams & Wilkins, Baltimore, 1995.

Blumenthal, J. A., et al. Effects of exercise training on older patients with major depression. Arch Intern Med. 1999, 159:2349-2356.

Bown. C. D. et al. Regulation of ER stress proteins by valproate: therapeutic implications. Bipolar Disorders 2002, 4: 145-151.

Caroff, S. N. eat al: Movement disorders associated with atypical antipsychotic drugs. J. Clin. Psychiatry. 2002; 63 (suppl 4) 12-19.

Chuang, D-M., et al. Neuroprotective effects of lithium in cultured cells and animal models of diseases. Bipolar Disorders 2002, 4: 129-136.

Deme, L. (Some aspects of children's linguistic education.) [in Hungarian] Tiszatáj (Szeged), 29, 1975, 16-21.

Deme, L. Personal communication. Káptalanfured, Hungary.

Duman, R. S., et al. Role of gene expression in stress and drug-induced neural plasticity. TEN (The Economics of Neuroscience), 2000;2(4), 53-70.

Duman. R. S. et al. Neural plasticity to stress and antidepressant treatment. Biol. Psychiatry 1999, 46: 1181-1191.

Duman. R. S. et al. Neural plasticity to stress and antidepressant treatment. Biol. Psychiatry 1999, 46: 1181-1191.

Fawcett cit#18: Please see citation 18 referenced in: Simon, R. I., 2002

Fazeli, M. S. et al. (eds) Cortical plasticity LTP and LTD. Bios Scientific Publishers, Oxford, 1996.

Forster P. Accurate assessment of short term suicide in a crisis. Psychiatric Annals 24:11, 1994 571-578.

Frankenburg, F. R. et al. Clozapine treatment of borderline patients: a preliminary study. Compr. Psychiatry. 1993, 34:402-405.

Gabbard, O. G. Integrated treatment of borderline personality disorder: Pharmacotherapy and psychotherapy. (video) 1995, American Psychiatric Press.

George, M. S. Introduction: the emerging neuroanatomy of depression. Psychiatric Annals, 24:12, 1994, 635-636.

George, M. S., et al. Activation studies in mood disorders. Psychiatric Annals, 24:12, 1994, 648-652.

Grisby, J., et al. Neurodynamics of personality, Guilford, New York, 2000.

Haney, C., et al "Interpersonal dynamics in a simulated prison". International Journal of Criminology and Penology, 1973, 1; 69-97.

Keck, P.E. et al.(2000 a) Antipsychotics in the treatment of mood disorders and risk of tardive dyskinesia. J. Clin. Psychiatry, 2000, Suppl. 4. 33-38.

Lee, A. L., et al. Stress and depression: possible links to neuron death in the hippocampus. Bipolar Disorders 2002, 4: 117-128.

Lee, A. L., et al. Stress and depression: possible links to neuron death in the hippocampus. Bipolar Disorders 2002, 4: 117-128.

Li, X., et al. Glycogen synthase kinase-3β, mood stabilizers, and neuroprotection. Bipolar Disorders 2002, 4: 137-144.

Manji. K. H. (editorial). Structural plasticity and neuronal resilience: are these targets for mood stabilizers and antidepressants in the treatment of bipolar disorder? Bipolar Disorders 2002, 4: 77-79.

Miller, D. S. et al. Comparative efficacy of typical and atypical antipsychotics as add-on therapy to mood stabilizers in the treatment of acute mania. J. Clin. Psychiatry, 62:12, 975-980. 2001.

O'Connor, R. Active treatment of depression. WW Norton & Company, New York, 2001.

Restak, R., The secret life of the brain. Dana Press and Joseph Henry Press 2001.

Rotrosen, J., et al: The importance of Side effects in the development of new antipsychotic drugs. Psychiatric Annals. 25:5, 1995, 306-310.

Rubin, E. et al. Brain imaging studies of antidepressant treatments. Psychiatric Annals, 24:12, 1994, 653-658.

Russo-Neustadt, A., et al. Exercise, antidepressant medications, and enhanced brain derived neurotrophic factor expression. Neuropsychopharmacology, 1999, 21:5, 679-682.

Sajatovic, M. et al. Quetiapine alone and added to mood stabilizers for serious mood disorders. J. Clin. Psychiatry, 62:9, 728-732. 2001.

Simon, R. I., Suicide risk assessment in Managed Care settings. Primary Psychiatry, April 2002; Vol 9. NO.4. 42-49.

Spitzer, M. The mind within the net. Models of learning, thinking, and acting. A Bradford Book, Cambridge, 1999.

Spitzer, M. The mind within the net. Models of learning, thinking, and acting. A Bradford Book, Cambridge, 1999.

Thase, M. (2002 a): Comparing the methods used to compare antidepressants. Psychopharmacology Bulletin: Spring 2002-Vol. 36, Suppl.14-17

Thase, M. (2002 b): What role do atypical antipsychotic drugs have in treatment-resistant depression? J. Cin. Psychiatry 63:2, February 2002, 95-103.

Thase, M. (2002 c): Studying new antidepressants: if there were a light at the end of the tunnel, could we see it? J. Cin. Psychiatry 63 (suppl2) 2002, 24-28.

Thase, M. Treatment issues related to sleep and depression. J. Cin. Psychiatry 61; (suppl 11)2000, 46-50.

The Pennsylvania Health Care Cost Containment Council. Depression and other mood disorders in Southwestern Pennsylvania. July 2001. 1-169.

Tsai, SY. M., et al.: Risk factors for completed suicide in bipolar disorder. J. Clin Psychiatry. 2002:63:469-476.

Vogel, G. New brain cells prompt New theory of depression. Science. 290, 2000, 258-259.

Yardley, K. M. (1982 a) On distinguishing role plays from conventional methodologies. J. Theory Soc. Behaviour. 12; 1982, 125-139.

Yardley, K. M. (1982 b) On engaging actors in as-if experiments. Journal for the Theory of Social Behaviour. 12(3) 1982, 291-304.

Yatham, L. N. The role of novel antipsychotics in bipolar disorders. J. Clin Psychiatry; 63 (suppl. 3) 10-14. 2002.

Whereas particular embodiments of this invention have been described above for purposes of illustration, it will be evident to those skilled in the art that numerous variations of the details of the present invention may be made without departing from the invention as defined in the appending claims. This may include the addition of other medications.

REFERENCES

Adson, DE. Et al An open trial of quetiapine for anxiety in patients receiving an SSRI. Society of Biological Psychiatry Annual Meeting May 16-18, 2002, Philadelphia, Pa. (The research supported by AstraZeneca Pharmaceuticals, L. P.)

Alpert, J. E., et al.: Treatment-resistant depression: New alternatives. Current psychiatry Vol.1, No. 2. Feb., 2002. 11-20.

Arnt, J. et al Do novel antipsychotics have similar pharmacological characteristics? A review of the evidence. Neuropsychopharmacology, 1998, 18:63-101.

Ayd, F. et al. Psychostimulant (amphetamine or methylphenidate) therapy for chronic and treatment-resistant depression. 343-355. In: Zohar, J. et al. (eds). Treating resistant depression PMA publishing corp. New York, 1987.

Beck A, et al Cognitive therapy of depression Guilford Press New York 1979,

Beck, J. S, Cognitive therapy basics and beyond Guilford Press New York 1995,

Blier, P. et al Early onset of therapeutic action in depression and greater efficacy of antidepressant treatments: are they related? International Clinical Psychopharmacology 1997, 12(suppl3):S21-28.

Burns, D. Feeling good: The new mood therapy Avon Books New York, 1980

Bymaster, F. P. et al. Radioreceptor binding profile of the a typical antipsychotic olanzapine. Neuropsychopharmacology, 1996, 14:87-96.

Cohen, M. et al Tolerance to therapeutic effects of antidepressants. Am J Psychiatry 1985, 142, 489-490.

Cookson I. B. et al. Haloperidol in treatment of stutterers [letter]. Br J Psychiatry. 1973; 123:491.

DeBattista, C. et al 2003 Psychotropic dosing and monitoring guidelines Primary Psychiatry 2003, 10:80-84, 87-96

DiMascio, A. et al Effects of imipramine on individuals varying in level of depression. Amer J Psychiatry 1968, 124 (Supp8):55-58.

DSM IV-TR—Desk reference to the diagnostic criteria from DSM-IV-TR, American Psychiatric Association, Washington D.C. 2000.

Fava, G. A. Can long-term treatment with antidepressant drugs worsen the course of depression? J Clin Psychiatry 2003, 64:123-133.

Fux, M., et al. Emergence of depressive symptoms during treatment for panic disorder with specific 5-hydroxytryptophan reuptake inhibitors. Acta Psychiatr Scand 1993; 88:235-237.

Galdi J. The causality of depression in schizophrenia. Br J Psychiatry 1983, 142:621-625.

Garattini, S. Pharmacology of amineptine, an antidepressant agent acting on the dopaminergic system: a review. International Clinical Psychopharmacology 1997, 12(supp13): S15-S19.

Glenberg, A.J. How fast are antidepressants? J. Clin Psychiatry 2000, 61:712-721.

Harrow, M. et al. Depression in schizophrenia: Are neuroleptics, akinesia, or anhedonia involved? Schizophr Bull 1994, 20:327-338.

Hirschfeld, R. M. A. et al. Partial response and nonresponse to antidepressant therapy: current approaches and treatment options. J Clin Psychiatry, 2002; 63:826-837.

Hollister, L. E. et al. drug therapy of depression. Amitriptiline, perphenazine, and their combination in different syndromes. Arch. Gen. Psychiat. 17, 1967, 486-493.

Jenkins S. C. et al A pocket reference for psychiatrists American Psychiatric Press Washington D.C. 1990

Kane, J. M. The new antipsychotics. J Pract Psychiatry Behav Health.1997; 3:343-355.

Kaplan, H. I. et al. Kaplan and Sadock's Synopsis of Psychiatry ($8^{th\ edition}$) 1998 Williams & Wilkins, Baltimore Kaplan, M. Atypical antipsychotics for treatment of mixed depression and anxiety. J. Clin. Psychiatry 61:5, 388-389, 2000.

Lawler, C. P. et al. Interactions of the novel antipsychotic aripiprazole (OPC-14597) with dopamine and serotonin receptor subtypes. Neuropsychopharmacology 1999, 20:612-627.

Maguire, G. A. Prolactin elevation with antipsychotic medications: Mechanism of action and clinical consequences. J. Clin. Psychiatry 2002; 63 (Suppl 4) 56-62.

Montgomery S. A. Fast-onset antidepressants. International Clinical Psychopharmacology 1997, 12 (suppl 3):S1-5.

Nelson, J. C. The use of antipsychotic drugs in the treatment of depression. In: Treatment resistant depression. Zohar, J. et al. (eds) PMA publishing, New York, 1987.

Nelson, J. C. et al. A preliminary, open study of the combination of fluoxetine and desipramine for rapid treatment of major depression. Arch Gen Psychiatry 1991, 48:303-307.

Nierenberg, A. A. A systematic approach to treatment-resistant depression. J. Clin. Psychiatry Monograph series Vol. 10, NO.1 May 1992, 5-10.

O'Connor, M., et al. Adding risperidone to selective serotonin reuptake inhibitor improves chronic depression. J. Clin. Psychopharmacol. 18:1, 89-91, 1998.

Ohaeri, J. U. Naturalistic study of olanzapine in treatment-resistant schizophrenia and acute mania, depression and obsessional disorder. East African Medical Journal 2000, 77 86-92.

Ostroff, R. B. et al: Risperidone augmentation of selective serotonin reuptake inhibitors in major depression. J. Clin. Psychiatry. 1999; 60: 256-259.

Papp, M. et al. Pharmacological validation of the chronic mild stress model of depression. Eur J pharmacol 1996; 296: 129-136.

Papp, M. et al. Antidepressant-like activity of amisulpride in two animal models of depression. J Psychopharmacology, 2000, 14(1) 46-52.)

Parker, G., et al. Are the a typical antipsychotic drugs antidepressants? J. Clin. Psychopharmacol, 22:1 2002, 94-95.

Pitchot, W., et al. Addition of olanzapine for treatment-resistant depression. Am. J. Psychiatry, 158:10, 2001, 1737-1738.

Price, L. H. et al. Drug combination strategies. 197-222. In: Amsterdam, J. et al (eds). Treatment-resistant mood disorders. Cambridge University Press 2001.

Quitkin, F. M. et al. Does mirtazapine have a more rapid onset than SSRIs? J Clin Psychiatry 2001, 62:358-361.

Raskin A. et al Differential response to chlorpromazine, imipramine, and placebo. Arch Gen Psychiatry 1970, 23:164-173.

Robertson, M. M. et al. Major tranquillizers used as antidepressants: A review. Journal of affective disorders, 4, 173-193 1982.

Seeger. T. F. et al. Ziprasidone (CP-88,059): A new antipsychotic with combined dopamine and serotonin receptor antagonist activity. J Pharmacology and Experimental Therapeutics. 1995, 275:101-113.

Shelton, C. R., et al. A novel augmentation strategy for treating resistant major depression. Am J Psychiatry 158:1, January 2001 131-134

Szewczak, M. et al. The pharmacological profile of iloperidone, a novel a typical antipsychotic agent. Journal of Pharmacology and Experimental Therapeutics 1995, 274 (3): 1404-1413.

Thase, M. E. What role do a typical antipsychotic drugs have in treatment-resistant depression? J Clin Psychiatry 2002, 63:95-103.

Tollefson, G. D. et al. A double-blind, controlled comparison of the novel antipsychotic olanzapine versus haloperidol or placebo on anxious and depressive symptoms accompanying schizophrenia. Biol Psychiatry 1998; 43:803-810.

Yokoi, F. et al. Dopamine D2 and D3 receptor occupancy in normal humans treated with the antipsychotic drug aripiprazole (OPC 14597): A study using positron emission tomography and [11C]Raclopride. Neuropsychopharmacology 2002, 27:248-259.

Zimmerman, M., et al: Major depressive disorder and Axis I diagnostic comorbidity. J. Clin. Psychiatry 63:3, 2002; 187-183.

What is claimed is:

1. A method for treatment of a patient suffering from major depressive disorder, the said method comprising administering to said patient at a time selected from the group consisting of, as an initial treatment, as soon as possible and upon presentation of said patient to a physician or other health care provider an effective amount of an antidepressant, wherein said antidepressant is selected from the group consisting of serotonin reuptake inhibitors, selective norepinephrine reuptake inhibitors, combined action SSRI/SNRI, serotonin-2 antagonist/reuptake inhibitors, an antidepressant with alpha-2 antagonism plus serotonin-2 and serotonin-3 antagonism, an antidepressant with serotonin/norepinephrine/dopamine reuptake inhibition, an antidepressant with norepinephrine and dopamine reuptake inhibition, 5-HT-1alpha antagonist, 5-HT-1beta antagonist, 5-HT1A receptor agonists, 5-HT1A receptor agonists and antagonists, 5-HT2 receptor antagonists, viloxazine hydrochloride, dehydroepiandosterone, NMDA receptor antagonists, AMPA receptor potentiators, substance P antagonists/ neurokinin-1 receptor antagonists, nonpeptide Substance P antagonist, neurokinin 2 antagonists, neurokinin 3 antagonists, corticotropin-releasing factor receptor antagonists, antiglucocorticoid medications, glucocorticoid receptor antagonists, cortisol blocking agents, nitric oxide synthesize inhibitors, inhibitors of phosphodiesterase, enkephalinase inhibitors, GABA-A receptor agonists, free radical trapping agents, atypical MAOI's, selective MAOI inhibitors, hormones, folinic acid, leucovorin, tramadol, and tryptophan in combination with an antipsychotic drug, wherein said antipsychotic drug is selected from the group consisting of an atypical antipsychotic drug, and a dopamine system stabilizer, and wherein said major depressive disorder categorized as non-treatment resistant and non-psychotic.

2. A method for treatment of a patient suffering from unipolar depression, the said method comprising administering to said patient at a time selected from the group consisting of, as an initial treatment, as soon as possible and upon presentation of said patient to a physician or other health care provider an effective amount of an antidepressant, wherein said antidepressant is selected from the group consisting of serotonin reuptake inhibitors, selective norepinephrine reuptake inhibitors, combined action SSRI/SNRI, serotonin-2 antagonist/reuptake inhibitors, an antidepressant with alpha-2 antagonism plus serotonin-2 and serotonin-3 antagonism, an antidepressant with serotonin/norepinephrine/dopamine reuptake inhibition, an antidepressant with norepinephrine and dopamine reuptake inhibition, 5-HT-1alpha antagonist, 5-HT-1beta antagonist, 5-HT1A receptor agonists, 5-HT1A receptor agonists and antagonists, 5-HT2 receptor antagonists, viloxazine hydrochloride, dehydroepiandosterone, NMDA receptor antagonists, AMPA receptor potentiators, substance P antagonists/ neurokinin-1 receptor antagonists, nonpeptide Substance P antagonist, neurokinin 2 antagonists, neurokinin 3 antagonists, corticotropin-releasing factor receptor antagonists, antiglucocorticoid medications, glucocorticoid receptor antagonists, cortisol blocking agents, nitric oxide synthesize inhibitors, inhibitors of phosphodiesterase, enkephalinase inhibitors, GABA-A receptor agonists, free radical trapping agents, atypical MAOI's, selective MAOI inhibitors, hormones, folinic acid, leucovorin, tramadol, and tryptophan in combination with an antipsychotic drug, wherein said antipsychotic drug is selected from the group consisting of an atypical antipsychotic drug, and a dopamine system stabilizer, and wherein said unipolar depression categorized as non-treatment resistant and non-psychotic.

3. The method of claims 1 or 2 wherein said antipsychotic drug is an atypical antipsychotic.

4. The method of claim 3 wherein said atypical antipsychotic drug is selected from the group consisting of quetiapine, risperidone, ziprasidone, and pharmaceutically acceptable salts thereof.

5. The method of claim 3 wherein said atypical antipsychotic drug is selected from the group consisting of olanzapine, iloperidone, melperone, amperozide, and pharmaceutically acceptable salts thereof.

6. The method of claims 1 or 2 wherein said antipsychotic drug is a dopamine system stabilizer.

7. The method of claim 6, wherein said dopamine system stabilizer is aripiprazole, or pharmaceutically acceptable salts thereof.

8. The method of claims 1 or 2 wherein said antidepressant is selected from the group consisting of fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine, alaproclate and pharmaceutically acceptable salts thereof, and wherein said atypical antipsychotic drug is selected from the group consisting of risperidone, quetiapene, olanzapine, ziprasidone and aripiprazole.

9. The method of claims 1 or 2 wherein said antidepressant is selected from the group consisting of serotonin reuptake inhibitors, a selective norepinephrine reuptake inhibitors, combined action SSRI/SNRI, serotonin-2 antagonist/reuptake inhibitors, an antidepressant with alpha-2 antagonism plus serotonin-2 and serotonin-3 antagonism, an antidepressant with serotonin/norepinephrine/dopamine reuptake inhibition and an antidepressant with norepinephrine and dopamine reuptake inhibition.

10. The method of claims 1 or 2 wherein said antidepressant is selected from the group consisting of 5-HT-I alpha antagonist, 5-HT-I beta antagonist, 5-HTIA receptor agonists, 5-HTIA receptor agonists and antagonists, 5-HT2 receptor antagonists, viloxazine hydrochloride, dehydroepiandosterone, NMDA receptor antagonists, AMPA receptor potentiators, substance P antagonists/neurokinin-1 receptor antagonists, nonpeptide Substance P antagonist, neurokinin 2 antagonists, neurokinin 3 antagonists, corticotropin-releasing factor receptor antagonists, antiglucocorticoid medications, glucocorticoid receptor antagonists, cortisol blocking agents, nitric oxide synthesize inhibitors, inhibitors of phosphodiesterase, enkephalinase inhibitors, GABA-A receptor agonists, free radical trapping agents, atypical MAOI's, selective MAOI inhibitors, hormones, folinic acid, leucovorin, tramadol, and tryptophan.

11. The method of claims 1 or 2 wherein said antidepressant is a selective serotonin reuptake inhibitor.

12. The method of claim 9, wherein said antidepressant is selected from the group consisting of fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine, alaproclate and pharmaceutically acceptable salts thereof.

13. The method of claim 9, wherein said antidepressant is clomipramine.

14. The method of claim 8, wherein said antidepressant is fluoxetine and said antipsychotic is risperidone.

15. The method of claim 8, wherein said antidepressant is fluoxetine and said antipsychotic is quetiapine.

16. The method of claim 8, wherein said antidepressant is fluoxetine and said antipsychotic is olanzapine.

17. The method of claim 8, wherein said antidepressant is fluoxetine and said antipsychotic is aripiprazole.

18. The method of claim 8, wherein said antidepressant is paroxetine and said antipsychotic is risperidone.

19. The method of claim 8, wherein said antidepressant is paroxetine and said antipsychotic is quetiapine.

20. The method of claim 8, wherein said antidepressant is paroxetine and said antipsychotic is olanzapine.

21. The method of claim 8, wherein said antidepressant is paroxetine and said antipsychotic is aripiprazole.

22. The method of claim 8, wherein said antidepressant is sertraline and said antipsychotic is risperidone.

23. The method of claim 8, wherein said antidepressant is sertraline and said antipsychotic is quetiapine.

24. The method of claim 8, wherein said antidepressant is sertraline and said antipsychotic is olanzapine.

25. The method of claim 8, wherein said antidepressant is sertraline and said antipsychotic is aripiprazole.

26. The method of claim 8, wherein said antidepressant is fluvoxamine and said antipsychotic is risperidone.

27. The method of claim 8, wherein said antidepressant is fluvoxamine and said antipsychotic is quetiapine.

28. The method of claim 8, wherein said antidepressant is fluvoxamine and said antipsychotic is olanzapine.

29. The method of claim 8, wherein said antidepressant is fluvoxamine and said antipsychotic is aripiprazole.

30. The method of claim 8, wherein said antidepressant is fluoxetine and said antipsychotic is ziprasidone.

31. The method of claim 8, wherein said antidepressant is paroxetine and said antipsychotic is ziprasidone.

32. The method of claim 8, wherein said antidepressant is sertraline and said antipsychotic is ziprasidone.

33. The method of claim 8, wherein said antidepressant is fluvoxamine and said antipsychotic is ziprasidone.

34. The method of claim 8, wherein said antipsychotic is selected from the group consisting of risperidone, quetiapene, olanzapine, ziprasidone and aripiprazole, and the effective amount per day is from 0.5 mg to 4 mg for risperidone, from 25 mg to 400 mg for quetiapine, from 2.5 mg to 10 mg for olanzapine, from 10 mg to 40 mg for ziprasidone, and 2.5 mg to 15 mg for aripiprazole.

35. The method of claims 1 or 2 wherein an effective amount of said antidepressant is its recommended therapeutic dose, or its effective starting dose.

36. The method of claims 1 or 2 wherein the administration is oral.

37. The method of claims 1 or 2, wherein said treatment is given for resisting suicide.

38. The method of claim 2, wherein said treatment is effected for at least one of the group consisting of inhibiting the development of tolerance toward said antidepressant, remedying the development of tolerance toward said antidepressant, avoiding a paradoxical effect of said antidepressant sensitizing said patients to said depression, avoiding worsening of said depression from said antidepressant, and treating worsening of said depression from said antidepressant.

39. The method of claim 1, wherein said treatment is effected for at least one of the group consisting of inhibiting the development of tolerance toward said antidepressant, remedying the development of tolerance toward said antidepressant, avoiding a paradoxical effect of said antidepressant sensitizing said patients to said depression, avoiding worsening of said depression from said antidepressant, and treating worsening of said depression from said antidepressant.

40. The method of claim 11, wherein said antidepressant is selected from the group consisting of fluoxetine, norfluoxetine, paroxetine, sertraline, fluvoxamine, citalopram, escitalopram, zimelidine, indalpine, femoxetine, alaproclate and pharmaceutically acceptable salts thereof, and wherein said atypical antipsychotic drug is selected from the group consisting of risperidone, quetiapene, olanzapine, ziprasidone and aripiprazole.

41. The method of claim 11, wherein said antidepressant is clomipramine, and wherein said atypical antipsychotic drug is selected from the group consisting of risperidone, quetiapene, olanzapine, ziprasidone and aripiprazole.

42. The method of claim 2, wherein said treatment is effected for at least one of the group consisting of avoiding a paradoxical effect of said antidepressant sensitizing said patients to said depression, inhibiting worsening of said depression from said antidepressant, and treating worsening of said depression from said antidepressant.

43. The method of claim 1 wherein said treatment is effected for treating substantially all of said patients treated by said physician or other health care provider by said method, wherein said treatment is given for resisting suicide.

44. The method of claim 1 including treating a plurality of said patients by said method, wherein said antipsychotic drug is administered at a low dose, and said treatment is given for resisting suicide.

45. The method of claim 2 wherein said treatment is effected for treating substantially all of said patients treated by said physician or other health care provider by said method, and wherein said treatment is given for resisting suicide.

46. The method of claim 2 including treating a plurality of said patients by said method, wherein said antipsychotic drug is administered at a low dose, and said treatment is given for resisting suicide.

47. The method of claims 1, or 2, wherein said treatment is given for resisting suicide, and wherein said treatment is given for the benefit of the group of said patients being treated by said physician or health care provider.

48. The method of claim 43, 44, 45, or 46 wherein said treatment is given for the benefit of the group of said patients being treated by said physician or health care provider.

49. The method of claims 43 or 45, wherein said antipsychotic drug is an atypical antipsychotic.

50. The method of claims 43 or 45, wherein said atypical antipsychotic drug is selected from the group consisting of quetiapine, risperidone, ziprasidone, and pharmaceutically acceptable salts thereof.

51. The method of claims 43 or 45 wherein said atypical antipsychotic drug is selected from the group consisting of olanzapine, iloperidone, melperone, amperozide, and pharmaceutically acceptable salts thereof.

52. The method of claims 43 or 45 wherein said antipsychotic drug is a dopamine system stabilizer.

53. The method of 43 or 45 wherein said dopamine system stabilizer is aripiprazole, or pharmaceutically acceptable salts thereof.

54. The method of claims 43 or 45 wherein said antidepressant is selected from the group consisting of serotonin reuptake inhibitors, a selective norepinephrine reuptake inhibitors, combined action SSRI/SNRI, serotonin-2 antagonist/reuptake inhibitors, an antidepressant with alpha-2 antagonism plus serotonin-2 and serotonin-3 antagonism, an antidepressant with serotonin/norepinephrine/dopamine reuptake inhibition and an antidepressant with norepinephrine and dopamine reuptake inhibition.

55. The method of claims 43 or 45 wherein said antidepressant is selected from the group consisting of 5-HT-IaIpha antagonist, 5-HT-Ibeta antagonist, 5-HT1A receptor agonists, 5-HTIA receptor agonists and antagonists, 5-HT2 receptor antagonists, dehydroepiandosterone, NMDA receptor antagonists, AMPA receptor potentiators, substance P antagonists/neurokinin-1 receptor antagonists, nonpeptide Substance P antagonist, neurokinin 2 antagonists, neurokinin 3 antagonists, corticotropin-releasing factor receptor antagonists, antiglucocorticoid medications, glucocorticoid receptor antagonists, cortisol blocking agents, nitric oxide synthesize inhibitors, inhibitors of phosphodiesterase, enkephalinase inhibitors, GABA-A receptor agonists, atypical MAOI's, selective MAOI inhibitors, hormones, folinic acid, leucovorin, tramadol, and tryptophan.

56. The method of claims 43 or 45 wherein said antidepressant is a selective serotonin reuptake inhibitor.

57. The method of 43 or 45 wherein said antidepressant is selected from the group consisting of fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine, alaproclate and pharmaceutically acceptable salts thereof.

58. The method of 43 or 45 wherein said antidepressant is clomipramine.

59. The method of claims 43 or 45 wherein said antidepressant is fluoxetine and said antipsychotic is risperidone.

60. The method of claims 43 or 45 wherein said antidepressant Is fluoxetine and said antipsychotic is quetiapine.

61. The method of claims 43 or 45 wherein said antidepressant is fluoxetine and said antipsychotic is olanzapine.

62. The method of claims 43 or 45 wherein said antidepressant is fluoxetine and said antipsychotic is aripiprazole.

63. The method of claims 43 or 45 wherein said antidepressant is paroxetine and said antipsychotic is risperidone.

64. The method of claims 43 or 45 whereto said antidepressant is paroxetine and said antipsychotic is quetiapine.

65. The method of claims 43 or 45 wherein said antidepressant is paroxetine and said antipsychotic is olanzapine.

66. The method of claims 43 or 45 wherein said antidepressant is paroxetine and said antipsychotic is aripiprazole.

67. The method of claims 43 or 45 wherein said antidepressant is sertraline and said antipsychotic is risperidone.

68. The method of claims 43 or 45 wherein said antidepressant is sertraline and said antipsychotic is quetiapine.

69. The method of claims 43 or 45 wherein said antidepressant is sertraline and said antipsychotic is olanzapine.

70. The method of claims 43 or 45 Wherein said antidepressant is sertraline and said antipsychotic is aripiprazole.

71. The method of claims 43 or 45 wherein said antidepressant is fluvoxamine and said antipsychotic is risperidone.

72. The method of claims 43 or 45 wherein said antidepressant is fluvoxamine and said antipsychotic is quetiapine.

73. The method of claims 43 or 45 wherein said antidepressant is fluvoxamine and said antipsychotic is olanzapine.

74. The method of claims 43 or 45 wherein said antidepressant is fluvoxamine and said antipsychotic is aripiprazole.

75. The method of claims 43 or 45 wherein said antidepressant is fluoxetine and said antipsychotic is ziprasidone.

76. The method of claims 43 or 45 wherein said antidepressant is paroxetine and said antipsychotic is ziprasidone.

77. The method of claims 43 or 45 whereto said antidepressant is sertraline and said antipsychotic is ziprasidone.

78. The method of claims 43 or 45 wherein said antidepressant is fluvoxamine and said antipsychotic is ziprasidone.

79. The method of claims 43 or 45 wherein said antipsychotic is selected from the group consisting of risperidone, quetiapene, olanzapine, ziprasidone and aripiprazole, and the effective amount per day is from 0.5 mg to 4 mg for risperidone, from 25 mg to 400 mg for quetiapine, from 2.5 mg to 10 mg for olanzapine, from 10 mg to 40 mg for ziprasidone, and 2.5 mg to 15 mg for aripiprazole.

80. The method of claims 43 or 45 wherein an effective amount of said antidepressant is its recommended therapeutic dose, or its effective starting dose.

81. The method of claims 43 or 45 wherein the administration is oral.

82. The method of claims 43 or 45 wherein said treatment is effected for at least one of the group consisting of delaying relapse; resisting relapse; and resisting the recurrence of said depression.

83. The method of claims 43 or 45 wherein said treatment is effected for at least one of the group consisting of protecting against the development of tolerance toward the antidepressant; and remedying the development of tolerance toward said antidepressant.

84. The method of claims 43 or 45 wherein said treatment is effected for at least one of the group consisting of avoiding a paradoxical effect of said antidepressant sensitizing said patients to said depression; treating a paradoxical effect of said antidepressant sensitizing said patients to said depression; for avoiding worsening of said depression from said antidepressant; and treating worsening of said depression from said antidepressant.

85. The method of claims 43 or 45 wherein said treatment is effected for at least one of the group consisting of avoiding a paradoxical effect of said antidepressant sensitizing said patients to said depression and causing suicide; avoiding a paradoxical effect of said antidepressant sensitizing said patients to said depression and causing suicidal ideation; treating a paradoxical effect of said antidepressant sensitizing said patients to said depression and causing suicide; treating a paradoxical effect of said antidepressant sensitizing said patients to said depression and causing suicidal ideation; avoiding worsening of said depression from said antidepressant and causing suicide; avoiding worsening of said depression from said antidepressant and causing suicidal ideation; treating worsening of said depression from said antidepressant and causing suicide; and treating worsening of said depression from said antidepressant and causing suicidal ideation.

86. The method of claims 43 or 45 wherein said treatment is given for providing a neuroprotective effect.

87. The method of claims 43 or 45 wherein said treatment is given for treating residual symptoms of said depression.

88. The method of claims 43 or 45 wherein said antidepressant is selected from the group consisting of fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine, alaproclate and pharmaceutically acceptable salts thereof.

89. The method of claims 43 or 45 wherein said antidepressant is clomipramine.

90. The method of claims 43 or 45 wherein said antidepressant is ketamine.

91. The method of claims 43 or 45 wherein said antidepressant is ketamine, and wherein said antipsychotic are selected from the group consisting of perphenazine, trifluoperazine, zotepine, flupenthixol, amisulpride, and sulpiride.

92. The method of claims 43 or 45 wherein said antidepressant is ketamine, and wherein said antipsychotic are selected from the group consisting of risperidone, quetiapine, olanzapine, ziprazidone, and aripriprazole, and the effective amount per day is from 0.5 mg to 4 mg for risperidone, from 25 mg to 400 mg for quetiapine, from 2.5 mg to 10 mg for olanzapine, from 10-40 mg for ziprazidone, and 2.5 mg to 15 mg for aripriprazole.

93. A method for treatment of a patient suffering from major depressive disorder, said method comprising administering to said patient an effective amount of an antidepressant, wherein said antidepressant is selected from the group consisting of fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine, alaproclate and pharmaceutically acceptable salts thereof, in combination with an antipsychotic drug, wherein said antipsychotic drug is selected from the group consisting of risperidone, quetiapene, olanzapine, ziprasidone and aripiprazole, said major depressive disorder categorized as non-treatment resistant and non-psychotic, and wherein said treatment is effected for at least one of the group consisting of delaying relapse; resisting relapse; and resisting the recurrence of said depression.

94. A method for treatment of a patient suffering from unipolar depression, said method comprising administering to said patient an effective amount of an antidepressant, wherein said antidepressant is selected from the group consisting of fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine, alaproclate and pharmaceutically acceptable salts thereof, in combination with an antipsychotic drug, wherein said antipsychotic drug is selected from the group consisting of risperidone, quetiapene, olanzapine, ziprasidone and aripiprazole, said unipolar depression categorized as non-treatment resistant and non-psychotic; and wherein said treatment is effected for at least one of the group consisting of delaying relapse; resisting relapse; and resisting the recurrence of said depression.

95. A method for treatment of a patient suffering from major depressive disorder, said method comprising administering to said patient an effective amount of an antidepressant, wherein said antidepressant is selected from the group consisting of fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine, alaproclate and pharmaceutically acceptable salts thereof, in combination with an antipsychotic drug, wherein said antipsychotic drug is selected from the group consisting of risperidone, quetiapene, olanzapine, ziprasidone and aripiprazole, said major depressive disorder categorized as non-treatment resistant and non-psychotic, and wherein said treatment is effected for at least one of the group consisting of protecting against development of tolerance toward said antidepressant; and remedying the development of tolerance toward said antidepressant.

96. A method for treatment of a patient suffering from unipolar depression, said method comprising administering to said patient an effective amount of an antidepressant, wherein said antidepressant is selected from the group consisting of fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine, alaproclate and pharmaceutically acceptable salts thereof, in combination with an antipsychotic drug, wherein said antipsychotic drug is selected from the group consisting of risperidone, quetiapene, olanzapine, ziprasidone and aripiprazole, said unipolar depression categorized as non-treatment resistant and non-psychotic; and wherein said treatment is effected for at least one of the group consisting of protecting against development of tolerance toward said antidepressant; and remedying the development of tolerance toward said antidepressant.

97. A method for treatment of a patient suffering from major depressive disorder, said method comprising administering to said patient an effective amount of an antidepressant, wherein said antidepressant is selected from the group consisting of fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine, alaproclate and pharmaceutically acceptable salts thereof, in combination with an antipsychotic drug, wherein said antipsychotic drug is selected from the group consisting of risperidone, quetiapene, olanzapine, ziprasidone and aripiprazole, said major depressive disorder categorized as non-treatment resistant and non-psychotic, and wherein said treatment is effected for at least one of the group consisting of avoiding a paradoxical effect of said antidepressant -sensitizing said patients to said depression; treating a paradoxical effect of said antidepressant sensitizing said patients to .said depression; for avoiding worsening of said depression from said antidepressant; and treating worsening of said depression from said antidepressant.

98. A method for treatment of a patient suffering from unipolar depression, said method comprising administering to said patient an effective amount of an antidepressant, wherein said antidepressant is selected from the group consisting of fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine, alaproclate and pharmaceutically acceptable salts thereof, in combination with an antipsychotic drug, wherein said antipsychotic drug is selected from the group consisting of risperidone, quetiapene, olanzapine, ziprasidone and aripiprazole, said unipolar depression categorized as non-treatment resistant and non-psychotic; and wherein said treatment is effected for at least one of the group consisting of avoiding a paradoxical effect of said antidepressant sensitizing said patients to said depression; treating a paradoxical effect of said antidepressant sensitizing said patients to said depression; for avoiding worsening of said depression from said antidepressant; and treating worsening of said depression from said antidepressant.

99. a method for treatment of a patient suffering from major depressive disorder, said method comprising administering to said patient an effective amount of an antidepressant, wherein said antidepressant is selected from the group consisting of fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine, alaproclate and pharmaceutically acceptable salts thereof, in combination with an antipsychotic drug, wherein said antipsychotic drug is selected from the group consisting of risperidone, quetiapene, olanzapine, ziprasidone and aripiprazole, said major depressive disorder categorized as non-treatment resistant and non-psychotic, and wherein said treatment is effected for at least one of the group consisting of avoiding a paradoxical effect of said antidepressant sensitizing said patients to said depression and causing suicide; avoiding a paradoxical effect of said antidepressant sensitizing said patients to said depression and causing suicidal ideation; treating a paradoxical effect of said antidepressant sensitizing said patients to said depression and causing suicide; treating a paradoxical effect of said antidepressant sensitizing said patients to said depression and causing suicidal ideation; avoiding worsening of said depression from said antidepressant and causing suicide; avoiding worsening of said depression from said antidepressant and causing suicidal ideation; treating worsening of said depression from said antidepressant and causing suicide; and treating worsening of said depression from said antidepressant and causing suicidal ideation.

100. A method for treatment of a patient suffering from unipolar depression, said method comprising administering to said patient an effective amount of an antidepressant, wherein said antidepressant is selected from the group consisting of fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine, alaproclate and pharmaceutically acceptable salts thereof, in combination with an antipsychotic drug, wherein said antipsychotic drug is selected from the group consisting of risperidone, quetiapene, olanzapine, ziprasidone and aripiprazole, said unipolar depression categorized as non-treatment resistant and non-psychotic; and wherein said treatment is effected for at least one of the group consisting of avoiding a paradoxical effect of said antidepressant sensitizing said patients to said depression and causing suicide; avoiding a paradoxical effect of said antidepressant sensitizing said patients to said depression and causing suicidal ideation; treating a paradoxical effect of said antidepressant sensitizing said patients to said depression and causing suicide; treating a paradoxical effect of said antidepressant sensitizing said patients to said depression and causing suicidal ideation; avoiding worsening of said depression from said antidepressant and causing suicide; avoiding worsening of said depression from said antidepressant and causing suicidal ideation; treating worsening of said depression from said antidepressant and causing suicide; and treating worsening of said depression from said antidepressant and causing suicidal ideation.

101. A method for treatment of a patient suffering from major depressive disorder, said method comprising administering to said patient an effective amount of an antidepressant, wherein said antidepressant is selected from the group consisting of fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine, alaproclate and pharmaceutically acceptable salts thereof, in combination with an antipsychotic drug, wherein said antipsychotic drug is selected from the group consisting of risperidone, quetiapene, olanzapine, ziprasidone and aripiprazole, said major depressive disorder categorized as non-treatment resistant and non-psychotic, and wherein said treatment is given for treating residual symptoms of said depression.

102. A method for treatment of a patient suffering from unipolar depression, said method comprising administering to said patient an effective amount of an antidepressant, wherein said antidepressant is selected from the group consisting of fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine, alaproclate and pharmaceutically acceptable salts thereof, in combination with an antipsychotic drug, wherein said antipsychotic drug is selected from the group consisting of risperidone, quetiapene, olanzapine, ziprasidone and aripiprazole, said unipolar depression categorized as non-treatment resistant and non-psychotic; and wherein said treatment is given for treating residual symptoms of depression.

103. A method for treatment of a patient suffering from unipolar depression, said method comprising administering to said patient an effective amount of an antipsychotic drug wherein said antipsychotic drug is selected from the group consisting of an atypical antipsychotic drug, and a dopamine system stabilizer, wherein said treatment is effected for resisting suicide, and wherein said unipolar depression categorized as non-treatment resistant and non-psychotic.

104. The method of claim 103, wherein said treatment is effected for at least one of the group consisting of avoiding a paradoxical effect of antidepressant sensitizing patients to depression; treating a paradoxical effect of antidepressant sensitizing patients to depression; for avoiding worsening of depression from the antidepressant; and treating worsening of depression from the antidepressant.

105. The method of claim 103, wherein said treatment is effected at a time selected from the group consisting of, as an initial treatment, as soon as possible and upon presentation of said patient to a physician or other health care provider, and wherein said atypical antipsychotic drug or said dopamine system stabilizer is administered at a low dose.

106. The method of claim 103 104, or 105, wherein said atypical antipsychotic or said dopamine system stabilizer is selected from the group consisting of risperidone, olanzapine, ziprasidone and aripiprazole, and the effective amount per day is from 0.5 mg to 4 mg for risperidone, from 2.5 mg to 10 mg for olanzapine, from 10 mg to 40 mg for ziprasidone, and 2.5 mg to 15 mg for aripiprazole.

107. The method of claim 103, 104, or 105, wherein said atypical antipsychotic is quetiapene, and the effective amount per day is from 25 mg to 400 mg.

108. The method of claim 8, wherein said treatment is selected as the first choice of treatment, and said treatment is effected for resisting suicide.

109. A method for treatment of a patient having cognitive distortions with functional impairment or health hazards, wherein said patient is suffering from major depressive disorder, wherein said major depressive disorder categorized as non-treatment resistant and non-psychotic, wherein said method comprising administering to said patient an effective amount of an antidepressant, wherein said antidepressant is selected from the group consisting of serotonin reuptake inhibitors, a selective norepinephrine reuptake inhibitors, combined action SSRI/SNRI, serotonin-2 antagonist/reuptake inhibitors, an antidepressant with alpha-2 antagonism plus serotonin-2 and serotonin-3 antagonism, an antidepressant with serotonin/norepinephrine/dopamine reuptake inhibition, an antidepressant with norepinephrine and dopamine reuptake inhibition, 5-HT-1alpha antagonist, 5-HT-1beta antagonist, 5-HT1A receptor agonists, 5-HT1A receptor agonists and antagonists, 5-HT2 receptor antagonists, viloxazine hydrochloride, dehydroepiandosterone, NMDA receptor antagonists, AMPA receptor potentiators, substance P antagonists/ neurokinin-1 receptor antagonists, nonpeptide Substance P antagonist, neurokinin 2 antagonists, neurokinin 3 antagonists, corticotropin-releasing factor receptor antagonists, antiglucocorticoid medications, glucocorticoid receptor antagonists, cortisol blocking agents, nitric oxide synthesize inhibitors, inhibitors of phosphodiesterase, enkephalinase inhibitors, GABA-A receptor agonists, free radical trapping agents, atypical MAOI's, selective MAOI inhibitors, hormones, folinic acid, leucovorin, tramadol, and tryptophan in combination with an antipsychotic drug, wherein said antipsychotic drug is selected from the group consisting of a typical antipsychotic drug, an atypical antipsychotic drug, and a dopamine system stabilizer.

110. A method for treatment of a patient having cognitive distortions with functional impairment or health hazards, wherein said patient is suffering from major depressive disorder, wherein said major depressive disorder categorized as non-treatment resistant and non-psychotic, wherein the method comprising administering to said patient an antipsychotic drug, wherein said antipsychotic drug is selected from the group consisting of an atypical antipsychotic drug, and a dopamine system stabilizer and wherein said treatment is effected for resisting suicide.

111. The method of claim 110, wherein said treatment is effected for at least one of the group consisting of avoiding a paradoxical effect of antidepressant sensitizing patients to depression; treating a paradoxical effect of antidepressant sensitizing patients to depression; for avoiding worsening of depression from the antidepressant; and treating worsening of depression from the antidepressant.

112. The method of claim 110, wherein said treatment is effected at a time selected from the group consisting of, as an initial treatment, as soon as possible and upon presentation of said patient to a physician or other health care provider, and wherein said atypical antipsychotic drug or said dopamine system stabilizer is administered at a low dose.

113. The method of claims 109, 110, or 111 wherein said atypical antipsychotic or said dopamine system stabilizer is selected from the group consisting of risperidone, quetiapene, olanzapine, ziprasidone and aripiprazole, and the effective amount per day is from 0.5 mg to 4 mg for risperidone, from 25 mg to 400 mg for quetiapine, from 2.5 mg to 10 mg for olanzapine, from 10 mg to 40 mg for ziprasidone, and 2.5 mg to 15 mg for aripiprazole.

114. A method for treatment of a patient suffering from major depressive disorder, the said method comprising administering to said patient at a time selected from the group consisting of, as an initial treatment, as soon as possible and upon presentation of said patient to a physician or other health care provider an effective amount of an antidepressant, wherein said antidepressant is an antidepressant excluding tricyclic antidepressants, tetracyclic antidepressants and permanent inhibitors of monoamine oxidase and wherein said antidepressant is selected from an antidepressant with final common pathway of antidepressant action associated with the NMDA receptor complex, inducing adaptive changes in the glycine regulatory sites of the NMDA receptor producing a 2-4 fold reduction in the glycine to inhibit 5,7-DCKA binding to the NMDA receptor-associated glycine sites, wherein said antidepressant is used in combination with an antipsychotic drug, wherein said antipsychotic drug is selected from the group consisting of a typical antipsychotic drug, an atypical antipsychotic drug, and a dopamine system stabilizer, and wherein said major depressive disorder categorized as non-treatment resistant and non-psychotic.

115. A method for treatment of a patient suffering from unipolar depression, the said method comprising administering to said patient at a time selected from the group consisting of, as an initial treatment, as soon as possible and upon presentation of said patient to a physician or other health care provider an effective amount of an antidepressant, wherein said antidepressant is an antidepressant excluding tricyclic antidepressants, tetracyclic antidepressants and permanent inhibitors of monoamine oxidase and wherein said antidepressant is selected from an antidepressant with final common pathway of antidepressant action associated with the NMDA receptor complex, inducing adaptive changes in the glycine regulatory sites of the NMDA receptor producing a 2-4 fold reduction in the glycine to inhibit 5,7-DCKA binding to the NMDA receptor-associated glycine sites and wherein said antidepressant is used in combination with an antipsychotic drug, wherein said antipsychotic drug is selected from the group consisting of a typical antipsychotic drug, an atypical antipsychotic drug, and a dopamine system stabilizer, and wherein said unipolar depression categorized as non-treatment resistant and non-psychotic.

116. The method of claims 114 or 115 wherein said atypical antipsychotic drug is selected from the group consisting of quetiapine, risperidone, ziprasidone, olanzapine, iloperidone, melperone, amperozide, and pharmaceutically acceptable salts thereof.

117. The method of claims 114 or 115 wherein said dopamine system stabilizer is aripiprazole, or pharmaceutically acceptable salts thereof.

118. The method of claim 114, or 115, wherein said treatment is effected for at least one of the group consisting of inhibiting the development of tolerance toward said antidepressant, remedying the development of tolerance toward said antidepressant, avoiding a paradoxical effect of said antidepressant sensitizing said patients to said depression, avoiding worsening of said depression from said antidepressant, and treating worsening of said depression from said antidepressant.

119. The method of claim 114, or 115, wherein said treatment is given for resisting suicide.

120. The method of claim 114, or 115, wherein said treatment is effected for treating substantially all of said patients treated by said physician or said other health care provider by said method, and wherein said treatment is given for resisting suicide.

121. The method of claim 114, or 115, wherein said treatment is given for resisting suicide, and wherein said treatment is given for the benefit of the group of said patients being treated by said physician or health care provider.

122. The method of claim 1, 2, 114, or 115, wherein a physician or other health care provider is involving said patient in the decision-making of said method by discussing with said patient the risks/benefits, side effects of the medications, wherein discussion of why we cannot continue to refrain using said method is selected from the group comprising at least one of the following steps (a) wherein a said physician or said other health care provider is taking into account the risk/benefit for a group not just for an individual for said combination use of said antidepressants and said antipsychotics, (b) wherein a said physician or said other health care provider in further support of said decision-making of said method is drawing examples for said step (a) selected from the group consisting of (b-1) of how said healthcare providers were treating appendicitis, (b-2) how said healthcare providers are following similar procedures when giving thiamin routinely for everybody in the emergency room before giving intravenous glucose therefore preventing Korsakoff's syndrome in alcoholics, and (b-3) how said healthcare providers are routinely testing for drug screen in the emergency room even when the patient says that he or she is absolutely not taking any illicit drugs, therefore said examples (a, b-1, b-2 and b-3) are pointing out that said taking into account the risk/benefit for a group not just for an individual is customary in the medical practice, is a standard procedure and good clinical practice, thus needs to be applied for said method, (c) wherein in this step a said physician or said other health care provider is pointing out that in starting treatment right away with said combination use of said antidepressants and said antipsychotics in all those who are clinically depressed, it is the decrease of suicide rate that is the paramount important factor, (d) and wherein in this step it is pointed out that in the medical profession it would not be fair to continue hiding under the excuses of the added risk of the potential side effects of the antipsychotic medications, specifically with the availability of some of the safer said atypical antipsychotics when in a separate diagnostic category from major depressive disorder, in borderline personality disorder said physicians were not afraid of using the combination of antidepressants with antipsychotic medications and when in comparison, said major depressive disorder has two to two and a half times more risk for committed suicide.

123. The method of claim 122, wherein a said physician or said other health care provider is discussing with said patient other added benefits from the said combination use of said antidepressants and said antipsychotics wherein said added benefits of said treatment is effected for at least one of the group consisting of inhibiting disease progression, modifying the course of said major depressive disorder, inhibiting the development of tolerance toward said antidepressant, remedying the development of tolerance toward said antidepressant, avoiding a paradoxical effect of said antidepressant sensitizing said patients to said major depressive disorder, avoiding worsening of said major depressive disorder from said antidepressant, treating worsening of said major depressive disorder from said antidepressant.

124. The method of claim 1, 2, 114, or 115, wherein the said method is used for the purposes selected from the group consisting of (a) resisting nonadherence to the prescribed medication, (b) resisting said patients discontinuing, said prescribed medication.

125. The method of claim 122, wherein a said physician or said other health care provider is discussing with said patient other reasons and other rationales for using the combination of said antidepressant and said antipsychotic medications in said major depression, wherein said other reasons and other rationales are selected from at least one of the group consisting of the following steps (a) retrospective analysis of suicide committers with major depression showed that many of them have received inadequate treatment (b) it had been shown that among the depressed patients who committed suicide many of them actually had psychotic depression that went unrecognized so they were not receiving antipsychotic medications, (c) cognitive distortions like jumping into conclusions without the analysis of the facts that is prematurely getting into conclusions are characteristic for depression and that it seems that there is an overlap between the cognitive distortions, the mini psychosis of borderline personality disorder, and the full blown psychosis of psychotics, all of them being out of touch with reality but in different degrees and that atypical antipsychotics may be useful for targeting the cognitive distortions that overlap with psychosis (d) and wherein in that step the role of cognitive distortions in hopelessness and suicide is discussed, as a study confirmed the predictive value of hopelessness in suicide, and that hopelessness is the greatest predictor of suicide risk beyond the first year, however suicide occurs in only five per cent of terminally ill patients and their greatest risk factor is untreated depression, therefore it is not hopelessness per se, but its perception, that is the cognitive distortion characteristic of depression, that seems to be the most important factor, and since for strong perceptual disturbances, said physicians had been using said antipsychotics, the adjunctive use of said antipsychotics with said antidepressants in the treatment of said major depressive disorders is supported.

126. The method of claims 122 or 125, wherein said method is used for the purposes selected from the group consisting of (a) resisting nonadherence to the prescribed medication, (b) resisting said patients discontinuing said prescribed medication.

127. A method for treatment of a patient suffering from major depressive disorder, the said method comprising administering to said patient at a time selected from the group consisting of, as an initial treatment, as soon as possible and upon presentation of said patient to a physician or other health care provider an effective amount of an antidepressant, wherein said antidepressant is a newer antidepressant, and wherein said newer antidepressant is defined as an antidepressant excluding tricyclic antidepressants, tetracyclic antidepressants and permanent inhibitors of monoamine oxidase in combination with an antipsychotic drug, and wherein said major depressive disorder categorized as non-treatment resistant and non-psychotic.

128. The method of claim 127, wherein said antidepressant is selected from the group consisting of fluoxetine, norfluoxetine, paroxetine, sertraline, fluvoxamine, citalopram, escitalopram, bupropion, nefazodone, mirtazapine, venlafaxine, duloxetine, milnacipran, reboxetine, zimelidine, indalpine, gepirone, femoxetine, alaproclate and pharmaceutically acceptable salts thereof, wherein said antipsychotic drug is selected from the group consisting of an atypical antipsychotic and a dopamine system stabilizer, wherein said atypical antipsychotic drug is selected from the group consisting of risperidone, quetiapene, olanzapine, ziprasidone iloperidone, melperone, amperozide, and pharmaceutically acceptable salts thereof, and wherein said dopamine system stabilizer is aripiprazole.

129. A method for treatment of a non-psychotic and non-depressed patient selected from the group consisting of (a) a patient having cognitive distortions with functional impairment or health hazards and (b) of a patient undergoing smoking cessation or nicotine withdrawal, wherein in either case (a) or (b) the method is comprising of administering to said non-psychotic and non-depressed patient an effective amount of a newer antidepressant, wherein said newer antidepressant is defined excluding tricyclic antidepressants, tetracyclic antidepressants and permanent inhibitors of monoamine oxidase in combination with an antipsychotic drug, wherein said antipsychotic drug is selected from the group consisting of an atypical antipsychotic and a dopamine system stabilizer, wherein said antipsychotic drug is administered at a low dose, and wherein said treatment is given for resisting suicide.

130. A method for treatment of a patient suffering from major depressive disorder, the method comprising administering to said patient an effective amount of an antidepressant in combination with an antipsychotic drug, wherein said antipsychotic drug is selected from the group consisting of an atypical antipsychotic drug, and a dopamine system stabilizer, and wherein said major depressive disorder categorized as non-treatment resistant and non-psychotic.

131. A method for treatment of a patient suffering from unipolar depression, the method comprising administering to said patient an effective amount of an antidepressant in combination with an antipsychotic drug, wherein said antipsychotic drug is selected from the group consisting of an atypical antipsychotic drug, and a dopamine system stabilizer, and wherein said unipolar depression categorized as non-treatment resistant and non-psychotic.

132. The method of claim 130 or 131, wherein treatment is given for resisting suicide.

133. The method of claim 131, wherein treatment is effected for at least one of the group consisting of inhibiting the development of tolerance toward the antidepressant, remedying the development of tolerance toward the antidepressant, avoiding a paradoxical effect of antidepressant sensitizing patients to depression, avoiding worsening of depression from the antidepressant, and treating worsening of depression from the antidepressant.

* * * * *